(12) United States Patent
Kisselev et al.

(10) Patent No.: US 8,455,431 B2
(45) Date of Patent: Jun. 4, 2013

(54) INHIBITORS OF THE TRYPSIN-LIKE SITE OF THE PROTEASOME AND METHODS OF USE THEREOF

(75) Inventors: Alexei Kisselev, West Lebanon, NH (US); Dmitry V. Filippov, Leiden (NL); Herman Overkleeft, Leiden (NL)

(73) Assignees: Trustees of Dartmout College, Hanover, NH (US); Leiden University, Leiden (NL)

(*) Notice: Subject to any disclaimer, the term of this patent is extended or adjusted under 35 U.S.C. 154(b) by 0 days.

(21) Appl. No.: 13/399,189

(22) Filed: Feb. 17, 2012

(65) Prior Publication Data

US 2012/0214732 A1 Aug. 23, 2012

Related U.S. Application Data

(60) Provisional application No. 61/444,164, filed on Feb. 18, 2011.

(51) Int. Cl.
*A61P 33/00* (2006.01)
(52) U.S. Cl.
USPC .......... 514/4.6; 514/127; 514/19.3; 514/20.1; 514/12.2
(58) Field of Classification Search
None
See application file for complete search history.

(56) References Cited

FOREIGN PATENT DOCUMENTS

WO    WO 2005076886 A2 * 8/2005

OTHER PUBLICATIONS

Portaro F et al "Design of kallidin-releasing tissue kallikrein inhibitors based on the specificities of the enzyme's binding subsites" Biochem J. 323:167-171. Published Apr. 1, 1997.*
Baldisserotto et al. "Glutamine Vinyl Ester Proteasome Inhibitors Selective for Trypsin-like (β2) Subunit" European Journal of Medicinal Chemistry 2007 42:586-592.
Baldisserotto et al. "N-terminal-prolonged Vinyl Ester-based Peptides as Selective Proteasome β1 Subunit Inhibitors" Bioorganic & Medicinal Chemistry 2009 17:5535-5540.
Britton et al. "Selective Inhibitor of Proteasome's Caspase-like Sites Sensitizes Cells to Specific Inhibition of Chymotrypsin-like Sites" Chemistry & Biology 2009 16:1278-1289.
Groll et al. "Crystal Structure of Epoxomicin:20S Proteasome Reveals a Molecular Basis for Selectivity of α', β'—Epoxyketone Proteasome Inhibitors" Journal of the American Chemical Society 2000 122:1237-1238.
Groll et al. "Probing Structural Determinants Distal to the Site of Hydrolysis that Control Substrate Specificity of the 20S Proteasome" Chemistry & Biology 2002 9:655-662.
Groll, M. and Huber, R. "Inhibitors of the Eukaryotic 20S Proteasome Core Particle: a Structural Approach" Biochimica et Biophysica Acta 2004 1695:33-44.
Harris et al. "Substrate Specificity of the Human Proteasome" Chemistry & Biology 2001 8:1131-1141.
Kim et al. "Proteasome Inhibition by the Natural Products Epoxomicin and Dihydroeponemycin: Insights into Specificity and Potency" Bioorganic & Medicinal Chemistry Letters 1999 9:3335-3340.
Kisselev, A. F. "Joining the Army of Proteasome Inhibitors"Chemistry & Biology 2008 15:419-421.
Kisselev, A. F. and Goldberg, A. L. "Monitoring Activity and Inhibition of 26S Proteasomes with Fluorogenic Peptide Substrates" Methods in Enzymology 2005 398:364-378.
Kisselev, A. F. and Goldberg, A. L. "Proteasome Inhibitors: from Research Tools to Drug Candidates" Chemistry & Biology 2001 8:739-758.
Loidl et al. "Bifunctional Inhibitors of the Trypsin-like Activity of Eukaryotic Proteasomes" Chemistry & Biology 1999 6(4):197-204.
Marastoni et al. "Peptidyl Vinyl Ester Derivatives: New Class of Selective Inhibitors of Proteasome Trypsin-like Activity" Journal of Medicinal Chemistry 2005 48:5038-5042.
McCormack et al. "Kinetic Studies of the Branched Chain Amino Acid Preferring Peptidase Activity of the 20S Proteasome: Development of a Continuous Assay and Inhibition by Tripeptide Aldehydes and *clasto*—Lactacystin β-Lactone" Biochemistry 1998 37:7792-7800.
Nazif, T. and Bogyo, M. "Global Analysis of Proteasomal Substrate Specificity Using Positional—scanning Libraries of Covalent Inhibitors" Proceedings of the National Academy of Sciences USA 2001 98(6):2967-2972.
Screen et al. "Nature of Pharmacophore Influences Active Site Specificity of Proteasome Inhibitors" The Journal of Biological Chemistry 2010 285(51):40125-40134.
Zhou et al. "Design and Synthesis of an Orally Bioavailable and Selective Peptide Epoxyketone Proteasome Inhibitor (PR-047)" Journal of Medicinal Chemistry 2009 52:3028-3038.

* cited by examiner

*Primary Examiner* — Cecilia J Tsang
*Assistant Examiner* — Zachary J Miknis
(74) *Attorney, Agent, or Firm* — Licata & Tyrell P.C.

(57) ABSTRACT

The present invention is an inhibitor of the trypsin-like β2/β2i sites of the proteasome. The inhibitor is characterized as being a peptide-based epoxyketone or vinyl sulfone that contains an arginine or 4-aminomethylene-L-phenylalanine at the C-terminus (i.e., at the P1 position). Methods for using the inhibitor to inhibit the activity of the β2/β2i site of a proteasome and treat a proteasome-mediated disease or condition are also described.

8 Claims, 2 Drawing Sheets

INHIBITORS OF THE TRYPSIN-LIKE SITE OF THE PROTEASOME AND METHODS OF USE THEREOF

This patent application claims the benefit of priority from U.S. Provisional Application Ser. No. 61/444,164 filed Feb. 18, 2011, the content of which is incorporated herein by reference in its entirety.

This invention was made with government support under contract number 5RO1CA124634-02 awarded by the National Cancer Institute. The government has certain rights in the invention.

INTRODUCTION

Background of the Invention

Proteasomes are proteolytic machines that are responsible for turnover of the majority of proteins in mammalian cells. The proteasome inhibitor bortezomib (VELCADE) is used for treatment of multiple myeloma, and at least five second-generation proteasome inhibitors including carfilzomib (PR-171) (Demo, et al. (2007) *Cancer Res.* 67:6383-91; O'Connor, et al. (2009) *Clin. Cancer Res.* 15:7085-91), NPI-0052 (Chauhan, et al. (2005) *Cancer Cell* 8:407-19), CEP-18770 (Piva, et al. (2008) *Blood* 111:2765-75), MLN-9708 (Kupperman, et al. (2010) *Cancer Res.* 70:1970-80), and ONX-0912 (PR-047)(Zhou, et al. (2009) *J. Med. Chem.* 52:3028-38) are in clinical testing.

Proteasomes have three different types of active sites, chymotrypsin-like ($\beta$5), trypsin-like ($\beta$2), and caspase-like ($\beta$1). Cells of the immune system express $\gamma$-interferon inducible immunoproteasomes, which have slightly different catalytic subunits, namely the $\beta$5i (LMP7), $\beta$2i (MECL1), and $\beta$1i (LMP2). Of these, the chymotrypsin-like sites ($\beta$5 and ($\beta$5i) have long been considered as the only suitable targets for drug development. Bortezomib and all drugs presently undergoing trials were developed to target these sites (Adams (2004) *Cancer Cell* 5:417-21). However, bortezomib, CEP-18770, and MLN-9708 co-target the caspase-like sites (Piva, et al. (2008) supra; Kupperman, et al. (2010) supra; Kisselev, et al. (2006) *J. Biol. Chem.* 281:8583-8590; Altun, et al. (2005) *Cancer Res.* 65:7896-901; Berkers, et al. (2005) *Nat. Methods* 2:357-62), whereas NPI-0052 co-targets trypsin-like and caspase-like sites (Chauhan, et al. (2005) supra). This raises the question of whether inhibition of these sites is important for the anti-neoplastic activity of these drugs. It has been demonstrated that, in most multiple myeloma cell lines, cytotoxicity of inhibitors does not correlate with inhibition of the chymotrypsin-like sites but does correlate with loss of specificity and onset of inhibition of the trypsin-like sites (Britton, et al. (2009) *Chem. Biol.* 16:1278-89). These data strongly suggest that the trypsin-like sites are important co-targets for anti-neoplastic agents (Britton, et al. (2009) supra). Cell-permeable inhibitors of these sites are needed to test this hypothesis.

Conventional efforts to develop specific inhibitors of the trypsin-like site have met with limited success to date. Most proteasome inhibitors are short N-terminally capped peptides with an electrophilic group at the C-terminus. This electrophile interacts, reversibly or irreversibly, with the catalytic N-terminal threonine of the proteasome active site. The peptide moiety of the inhibitor binds to the substrate binding pocket of the active site and is largely responsible for the specificity (Kisselev & Goldberg (2001) *Chem. Biol.* 8:739-758; Groll & Huber (2004) *Biochim. Biophys. Acta* 1695:33-44), although the specificity may be influenced by an electrophile (Screen, et al. (2010) *J. Biol. Chem.* 285:40125-40134). The trypsin-like sites cleave peptide bonds after a basic residue and it has been shown that the P3 substituent (Arg) of the $\beta$2 selective inhibitor Ac-Tyr-Arg-Leu-Asn-VS 1(SEQ ID NO:1) is of importance in selectivity enhancement (Harris, et al. (2001) *Chem. Biol.* 8:1131-41; Nazif & Bogyo (2001) *Proc. Natl. Acad. Sci. USA* 98:2967-2972; Groll, et al. (2002) *Chem. Biol.* 9:655-62). However, inclusion of basic residues in the P1 and P3 positions are challenging to synthesize and would be expected to render the inhibitor cell-impermeable. In this respect, the few $\beta$2-specific aldehydes (Loidl, et al. (1999) *Chem. Biol.* 6:197-204) and vinyl sulfones (Nazif & Bogyo (2001) supra; Groll, et al. (2002) supra) are not cell-permeable. A cell-permeable peptide vinyl ester (ve), HMB-VSL-VE 2, has been suggested to be a specific inhibitor of the trypsin-like sites (Marastoni, et al. (2005) *J. Med. Chem.* 48:5038-42; Baldisserotto, et al. (2007) *Eur. J. Med. Chem.* 42:586-592), but does not show inhibitory activity in conventional assays (Screen, et al. (2010) supra).

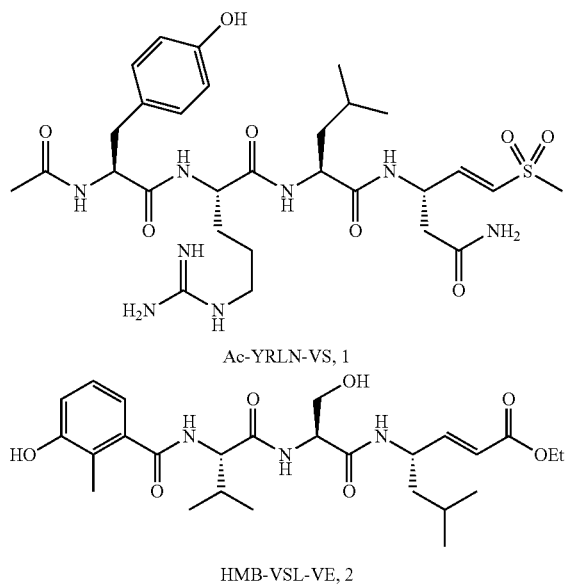

Ac-YRLN-VS, 1

HMB-VSL-VE, 2

SUMMARY OF THE INVENTION

The present invention a peptide-based inhibitor of the proteasome $\beta$2/$\beta$2i site having the structure:

(SEQ ID NO: 2)
(Y)-(X4)-X3-X2-X1, wherein X1 is an arginine residue or a 4-aminomethylene-L-phenylalanine residue with an epoxyketone or vinyl sulfone warhead; X2 is Leu or Ser, X3 is Leu, Val, Arg, or 4-aminomethylene-L-Phe, wherein X4 is present or absent and when present is Pro, Tyr, or Phe; and Y is present or absent and when present is a capping group. In certain embodiments, the inhibitor includes a label.

A pharmaceutical composition containing the peptide-based inhibitor of the invention and a pharmaceutically acceptable carrier is also provided, wherein some embodiments, embrace the inclusion of an inhibitor of the proteasome $\beta$5/$\beta$5i site.

Methods for inhibiting the activity of the β2/β2i site of a proteasome and treating cancer, allograft rejection, autoimmune disease, parasitic infection or inflammatory condition using the peptide-based inhibitor of the invention are also provided as is a method for producing a peptide-based inhibitor.

DETAILED DESCRIPTION OF THE INVENTION

Figure 1A:
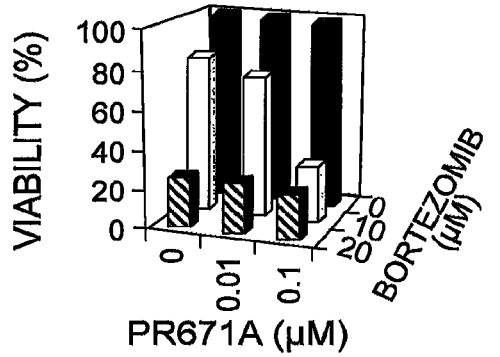
FIG. 1 shows that the combination of compound 4a (PR671A) with β5-selective proteasome inhibitors, bortezomib (FIGS. 1A and 1C) or PR523 (i.e., LU-005.
FIGS. 1B and 1D) results in synergistic cytoxicity against myeloma cells, U266 (FIGS. 1A and 1B) and AMO-1 (FIGS. 1C and 1D) cells.
Figure 1C:
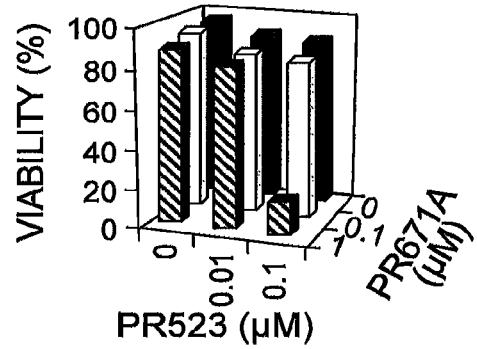
Figure 1B:
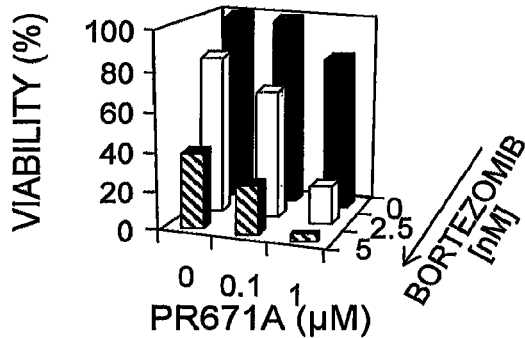
Figure 1D:
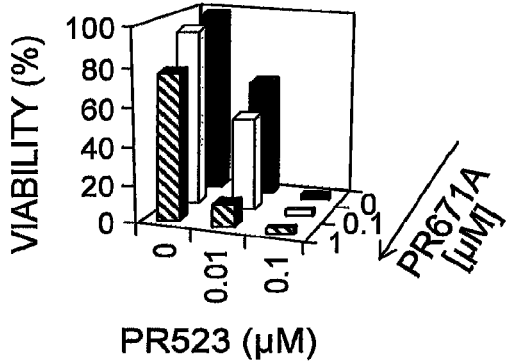

Proteasomes degrade the majority of proteins in mammalian cells, are involved in the regulation of multiple physiological functions, and are established targets of anti-cancer drugs. The mammalian 20S proteasome catalytic core contains two sets of three catalytically active β subunits, which display a different substrate specificity, namely β1 (caspase-like) cleaves after acidic residues, β2 (trypsin-like) cleaves after basic residues and β5 (chymotrypsin-like) cleaves after bulky, hydrophobic residues. In specific cell types involved in the immune surveillance system, the β1i, β2i and β5i active subunits replace their corresponding constitutive counterparts and, β5 is replaced by β5t in cortical thymic epithelial cells.

Chymotrypsin-like sites are the most important for protein breakdown and have been the primary target for anti-neoplastic drug development; however, inhibitors of caspase-like sites have also been shown to sensitize malignant cells to inhibitors of the chymotrypsin-like sites. In the instant invention, specific cell-permeable inhibitors and activity-based probes of the third site type, the trypsin-like sites, have now been developed. These compounds are peptide-based epoxyketones or vinyl sulfones (VS) that contain arginine or 4-aminomethylene-L-phenyalanine in the P1 position and inhibit trypsin-like β2/β2i sites of 26S proteasomes. The compounds of the invention also selectively sensitize multiple myeloma cells to inhibitors of the chymotrypsin-like sites, including the anti-myeloma agents bortezomib and carfilzomib. Sensitization was observed in cultured cells adapted to grow in the presence of bortezomib and bortezomib-resistant multiple myeloma cells isolated from patients with bortezomib-refractory myeloma. Thus, the compounds of the invention, when used in combination with inhibitors to the chymotryptic/caspase proteasome activity, overcome resistance of myeloma cells against these inhibitors. Thus, trypsin-like sites are co-targets (with chymotrypsin-like sites) for anti-cancers drugs and the compounds of this invention can be used in the treatment of cancer and sensitization of malignant cells to therapeutic proteasome inhibitors that target β5/β5i sites of the proteasome. Using the specific cell-permeable inhibitors and activity-based probes of this invention, the proteasome's active sites can be modulated separately in living cells.

Accordingly, the present invention features inhibitors of the trypsin-like β2/β2i sites of 26S proteasomes, which are characterized as being peptide-based epoxyketones or vinyl sulfones that contain an arginine or 4-amino-L-methylene-phenylalanine at the C-terminus (i.e., at the P1 position). Inhibitors of the present invention are "peptide-based" in the sense that they contain between 1 and 5 amino acid residues covalently attached by peptide bonds. In some embodiments, the inhibitors of the invention are oligopeptides containing between 2 and 5 amino acid residues. In other embodiments, the inhibitors of the invention are oligopeptides containing between 3 and 5 amino acid residues. In particular embodiments, the inhibitors of the invention are oligopeptides containing between 2 and 4 or 3 and 4 amino acid residues.

For the purposes of the present invention, an amino acid residue can be a natural amino acid residue or non-natural amino acid residue. Thus, the inhibitors of the invention can contain between 1 and 5 amino acid residues, wherein 1 to 5 of the amino acid residues are natural or non-natural amino acid residues.

The inhibitors of the invention have the general structure of:

$$(Y)-(X4)-X3-X2-X1, \quad \text{(SEQ ID NO: 2)}$$

wherein X1 is an arginine residue or 4-aminomethylene-L-phenylalanine residue, wherein said residue has an epoxyketone (ek) or vinyl sulfone (VS) warhead; X2 is Leu or Ser, X3 is Leu, Val, Ser, Arg, or 4-aminomethylene-L-Phe; X4 is present or absent and when present is Pro, Tyr, or Phe, and Y is present or absent and when present is a capping group.

A capping group of the present invention is a group routinely used in the art to cap or protect alpha amino groups. Capping groups of use in the instant invention include, but not limited to, a HMB (N-(3-hydroxy-2-methylbenzoyl)) group, an acetyl (Ac) group, a carboxybenzyl (Z) group, a benzoyl (Bz)group, or an azido group, See Kristjansson (2001) *Curr. Protoc. Food Anal. Chem.* C2.1.1-C2.1.7.

Detectable labels or dyes can also serve as capping groups of the instant peptides. Labels or dyes are detectable in the sense that they can be directly or indirectly measured by fluorometry, spectrometry or the like. Examples of amine-reactive dyes or labels which can serve as capping groups of the instant invention include, but are not limited to, a BODIPY fluorophore (e.g., BODIPY FL, BODIPY 493/503, BODIPY 530/550, BODIPY TMR, BODIPY 558/568, BODIPY 576/589, BODIPY 581/591, BODIPY TR, BODIPY 630/650, or BODIPY 650/665), an ALEXA Fluor (e.g., ALEXA Fluor 405, ALEXA Fluor 532, ALEXA Fluor 555, ALEXA Fluor 546, ALEXA Fluor 488 or ALEXA Fluor 750), a fluorescein (e.g., 2',7'-dichloro-fluoroscein, 4',5'-dichloro-2'7'-dimethoxyfluoroscein, or naphthofluorescein), a rhodamine dye (e.g., rhodamine red, X-rhodamineor a Texas Red dye), biotin and the like.

Exemplary peptide-based inhibitors of the invention include the molecules listed in Table 1.

TABLE 1

| Compound | SEQ ID NO: |
|---|---|
| NC-002 (Ac-Leu-Leu-Arg-ek) | |
| Az-NC-002 (AzGly-Leu-Leu-Arg-ek) | 3 |
| NC-012 (Ac-Arg-Leu-Arg-ek) | |

TABLE 1-continued
| Compound | SEQ ID NO: |
|---|---|
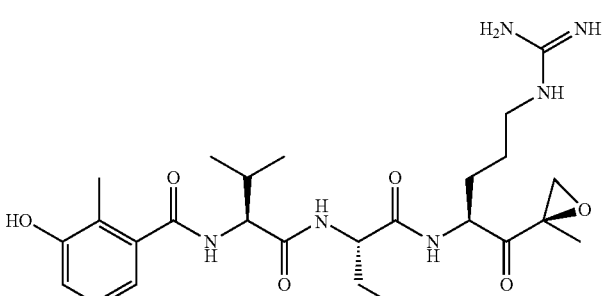
NC-022
(HMB-Val-Ser-Arg-ek)
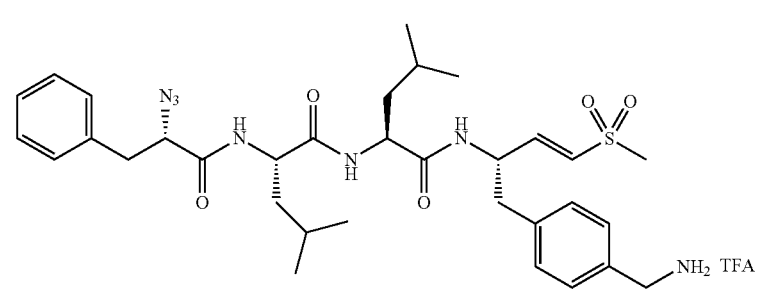 [SMILES: CC(C)C[C@H](NC(=O)[C@H](Cc1ccccc1)N=[N+]=[N-])C(=O)N[C@@H](CC(C)C)C(=O)N[C@H](/C=C/S(C)(=O)=O)Cc1ccc(CN)cc1]
4a (PR671A)
(N₃Phe-Leu-Leu-Phe(4-CH₂NH₂)VS)
4
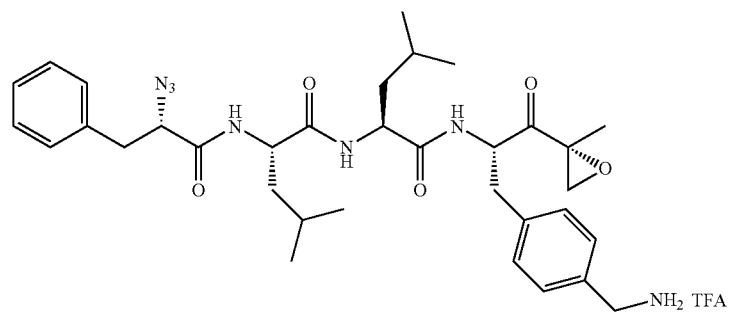 [SMILES: CC(C)C[C@H](NC(=O)[C@H](Cc1ccccc1)N=[N+]=[N-])C(=O)N[C@@H](CC(C)C)C(=O)N[C@@H](Cc1ccc(CN)cc1)C(=O)[C@@]1(C)CO1]
4b
(N₃Phe-Leu-Leu-Phe(4-CH₂NH₂)ek)
5
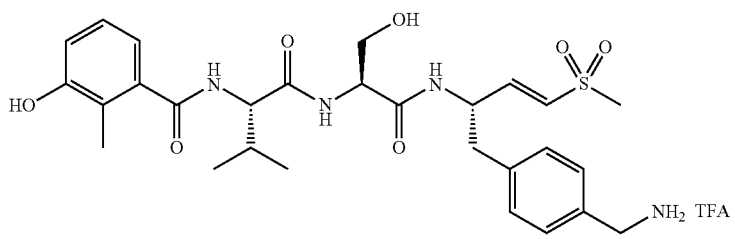 [SMILES: Cc1c(O)cccc1C(=O)N[C@H](C(=O)N[C@@H](CO)C(=O)N[C@H](/C=C/S(C)(=O)=O)Cc1ccc(CN)cc1)C(C)C]
40
((Val-Ser-Phe(4-CH₂NH₂)-methyl vinyl sulfone)-3-
hydroxy-2-methylbenzamide)

TABLE 1-continued

| Compound | SEQ ID NO: |
|---|---|
| 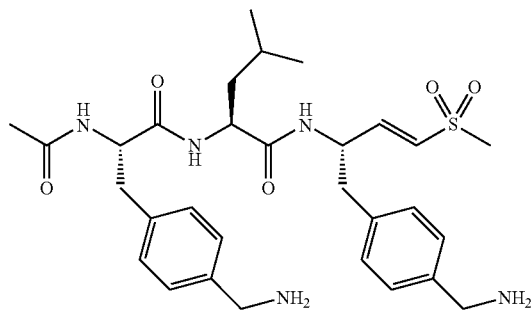 [SMILES: CC(=O)N[C@@H](Cc1ccc(CN)cc1)C(=O)N[C@@H](CC(C)C)C(=O)N[C@H](/C=C/S(C)(=O)=O)Cc1ccc(CN)cc1]  42<br>(Ac-Phe(4-CH$_2$NH$_2$)-Leu-Phe(4-CH$_2$NH$_2$)VS) | |
| 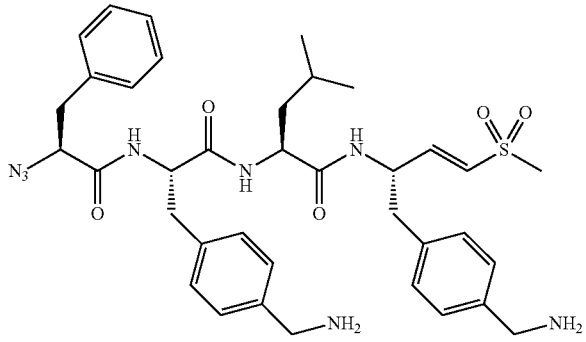 [SMILES: CC(C)C[C@H](NC(=O)[C@H](Cc1ccc(CN)cc1)NC(=O)[C@H](Cc1ccccc1)N=[N+]=[N-])C(=O)N[C@H](/C=C/S(C)(=O)=O)Cc1ccc(CN)cc1]  43<br>(N$_3$Phe-Phe(4-CH$_2$NH$_2$)-Leu-Phe(4-CH$_2$NH$_2$)VS) | 6 |
| 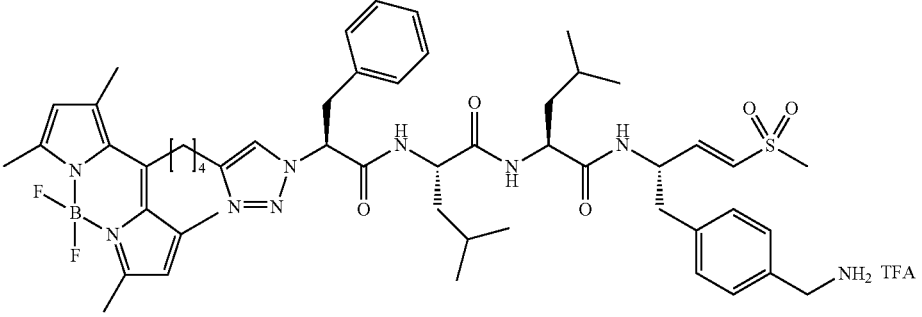  39<br>(BODIPY-triazole-Phe-Leu-Leu-Phe(4-CH$_2$NH$_2$)VS) | 7 |

Peptide-based inhibitors can be produced by the exemplary methods disclosed herein (see, e.g., Schemes 3-5 and the Examples), which, in general, involve the steps of (a) protecting amine groups of arginine or 4-aminomethylene-L-phenylalanine, (b) introducing an epoxyketone or vinyl sulfone warhead onto the arginine or 4-aminomethylene-L-phenylalanine, and (c) attaching a proteasomal β2/β2i site-selective oligopeptide to the alpha amino-group of the arginine or 4-aminomethylene-L-phenylalanine. As described herein, the P2, P3, and optional P4 amino acid residues of the peptide-based inhibitor are amino acid residues that enhance selectivity for the β2/β2i site of the proteasome. In this respect, "a proteasomal β2/β2i site-selective oligopeptide" is a peptide containing the P2, P3, and optional P4 amino acid residues as described herein.

Inhibitor compositions of this invention can be administered in various forms, depending on the disorder to be treated and the age, condition, and body weight of the subject, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional pharmaceutical carrier, additive or excipient, such as a binder, a disintegrating agent, a lubricant, a corrigent, a solubilizing agent, a suspension aid, an emulsifying agent, or a coating agent in addition to a cyclodextrin and a buffer. Although the dosage will vary depending on the symptoms, age and body weight of the patient, the nature and severity of the disorder to be treated or prevented, the route of administration and the form of the inhibitor, in general, a daily dosage of from 0.01 to 2000 mg of the inhibitor is recommended for an adult human patient, and this may be administered in a single dose or in divided doses. The amount of active ingredient which can be combined with a carrier material to produce a single dosage form will generally be that amount of the inhibitor which produces a therapeutic effect.

The precise time of administration and/or amount of a composition that will yield the most effective results in terms of efficacy of treatment in a given patient will depend upon the activity, pharmacokinetics, and bioavailability of a particular inhibitor, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is used herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

It is further contemplated that the instant inhibitors can be prepared as pharmaceutically acceptable salt. The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge, et al. (1977) *J. Pharm. Sci.* 66:1-19.)

In other cases, the inhibitors of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge, et al. (1977) supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent. Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (TWEENS, PLURONICS, sorbitan esters, lecithin, CREMOPHORS), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration can include one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle. Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of inhibitors may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion. The phrases "systemic administration," "administered systemically," "peripheral administration" and "administered peripherally" as used herein mean the administration of an inhibitor, or other material other than directly into the central nervous system, such that it enters the subject's system and thus, is subject to metabolism and other like processes, for example, subcutaneous administration.

The inhibitors of the invention may be administered to humans and other animals for therapy by any suitable route of administration, including orally, nasally, as by, for example, a spray, rectally, intravaginally, parenterally, intracistemally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The concentration of a disclosed inhibitor in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected inhibitor(s).

In one embodiment, the proteasome inhibitor is provided as a conjoint therapy, wherein one or more other therapeutic agents are administered with the proteasome inhibitor composition. Such conjoint treatment may be achieved by way of the simultaneous, sequential, or separate dosing of the individual components of the treatment.

In certain embodiments, a composition of the invention is conjointly administered with a chemotherapeutic. Suitable chemotherapeutics may include, natural products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; histone deacetylase (HDAC) inhibitors (trichostatin, sodium butyrate, apicidan, suberoyl anilide hydroamic acid); HSP90 inhibitors (i.e., tanespimycin, retaspimycin, AUY922) hormones (i.e., estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In other embodiments, a composition of the invention is conjointly administered with a cytokine. Cytokines include, but are not limited to, Interferon-γ, -α, and β, Interleukins 1-8, 10 and 12, Granulocyte Monocyte Colony-Stimulating factor (GM-CSF), TNF-α and -β, and TGF-β.

In still other embodiments, a composition of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a composition of the invention is conjointly administered with an immunotherapeutic agent. Suitable immunotherapeutic agents may include, but are not limited to, MDR modulators (verapamil, valspordar, biricodar, tariquidar, laniquidar), cyclosporine, thalidomide, lenalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

In particular embodiments, a composition of the invention is conjointly administered with one or more other proteasome inhibitor(s), in particular inhibitors of the chymotrypsin-like sites. Such inhibitors include, e.g., bortezomib (VELCADE), carfilzomib (PR-171), marizomib (NPI-0052), CEP-18770, MLN-9708, and ONX-0912 (PR-047).

Having demonstrated the selective activity of the instant inhibitors, the present invention features a method for inhibiting the $\beta2/\beta2i$ activity of proteasome by contacting a proteasome (either in vivo or in vitro) with a composition described herein. Activity of an inhibitor can be demonstrated using the exemplified cell-free or cell-based assays or any other suitable assay routinely used in the art to assess proteasome activity.

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations containing one or more of the proteasome $\beta2/\beta2i$-selective inhibitors described herein are of use in the treatment of these proteasome-mediated diseases or conditions. For the purposes of the present invention, a proteasome-mediated disease or condition is a disease or condition in which the activity or overactivity of the proteasome has been directly or indirectly associated with the development or persistence of the disease or condition. In this respect, inhibition of proteasome activity will have a beneficial effect of ameliorating, preventing or treating the disease or condition. In particular embodiments, the proteasome-mediated disease or condition is cancer, allograft rejection, autoimmune disease, parasitic infection or an inflammatory condition.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy (Glotzer, et al. (1991) *Nature* 349:132-138). The fact that epoxomicin was initially identified in a screen for antitumor compounds validates the proteasome as an antitumor chemotherapeutic target. Accordingly, the compositions of the invention are useful for treating cancer.

Proteasome inhibition has also been associated with inhibition of NF-κB activation and stabilization of p53 levels. Thus, compositions of the invention may also be used to inhibit NF-κB activation, and stabilize p53 levels in cell culture. Since NF-κB is a key regulator of inflammation, it is an attractive target for anti-inflammatory therapeutic intervention. Thus, compositions of the invention are of use in the treatment of conditions associated with inflammation, including, but not limited to COPD, psoriasis, bronchitis, emphysema, and cystic fibrosis.

The disclosed compositions can also be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include regulatory proteins such as cyclins and transcription factor NF-κB.

In some embodiment, the invention relates to the treatment of cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver.

Inhibitors of the invention are useful for treating conditions such as chronic infectious diseases, fever, muscle disuse (atrophy) and denervation, nerve injury, fasting, renal failure associated with acidosis, and hepatic failure. See, e.g., U.S. Pat. No. 5,340,736. Embodiments of the invention therefore encompass methods for reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a pharmaceutical composition disclosed herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κB2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB, which translocates from the cytoplasm to the nucleus. Ubiquitinated p105 is also processed by purified proteasomes (Palombella, et al. (1994) *Cell* 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κgene, the IL-2 receptor α-chain gene, the class I major histocompatibility complex gene, and a number of cytokine genes encoding, for example, IL-2, IL-6, granulocyte colony-stimulating factor, and IFN-β. (Palombella, et al. (1994) *Cell*

78:773-785). Thus, some embodiments of the invention include methods of affecting the level of expression of IL-2, MHC-I, IL-6, TNF-α, IFN-β, or any of the other previously-mentioned proteins, each method including administering to a subject an effective amount of a composition disclosed herein.

NF-κB also participates in the expression of the cell adhesion genes that encode E-selectin, P-selectin, ICAM, and VCAM-1 (Collins (1993) Lab. Invest. 68:499-508). Thus, one embodiment of the invention is a method for inhibiting cell adhesion (e.g., cell adhesion mediated by E-selectin, P-selectin, ICAM, or VCAM-1), including contacting a cell with (or administering to a subject) an effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor (Pye, et al. (2003) Am. J. Physiol. 284:H919-H926). Therefore, certain embodiments of the invention relate to a method of treating an ischemic condition or reperfusion injury by administering to a subject in need of such treatment an effective amount of a compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Overproduction of lipopolysaccharide (LPS)-induced cytokines such as TNF-α is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, indicating that the LPS-induced signal transduction may be an important therapeutic target in the treatment or prevention of sepsis (Qureshi, et al. (2003) J. Immun. 171:1515-1525). Therefore, in certain embodiments, compositions of the invention may be used for the inhibition of TNF-α to prevent and/or treat septic shock.

Many autoimmune diseases (e.g., lupus, myasthenia gravis) are mediated by the antibodies against self-produced by plasma cells. Just like malignant myeloma cells, plasma cells are very sensitive to proteasome inhibitors. Proteasome inhibitors deplete plasma cells in mouse models of these diseases (Neubert, et al. (2008) Nat. Med. 14:748-755). Accordingly, in one embodiment, the invention provides a method to treat an autoimmune disease by inducing selective apoptosis of autoantibody-producing plasma cells.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. A further embodiment is a method for suppressing the immune system of a subject (e.g., inhibiting transplant rejection, allergy, asthma), including administering to the subject an effective amount of a composition described herein. Compositions of the invention can also be used to treat autoimmune diseases such as lupus, rheumatoid arthritis, multiple sclerosis, and inflammatory bowel diseases such as ulcerative colitis and Crohn's disease.

Another further embodiment is a method for altering the repertoire of antigenic peptides produced by the proteasome or other N-terminal nucleophile (Ntn) with multicatalytic activity. For example, if the caspase-like (PGPH) activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of trypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. (1994) Cell 78:773-785; Traenckner, et al. (1994) EMBO J. 13:5433-5441). Thus, one embodiment of the invention is a method for inhibiting IκB-α degradation, including contacting the cell with a composition described herein. A further embodiment is a method for reducing the cellular content of NF-κB in a cell, muscle, organ, or subject, including contacting the cell, muscle, organ, or subject with a composition described herein.

Other embodiments of the invention are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with $p34^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover (1994) Cell 79:13-21). Inhibition of the proteasome inhibits cyclin degradation, and therefore inhibits cell proliferation, for example, in cyclin-related cancers (Kumatori, et al. (1990) Proc. Natl. Acad. Sci. USA 87:7071-7075). Thus, another embodiment of the invention is a method for treating a proliferative disease in a subject (e.g., cancer, psoriasis, or restenosis), including administering to the subject an effective amount of a composition disclosed herein. The invention also encompasses a method for treating cyclin-related inflammation in a subject, including adminstering to a subject a therapeutically effective amount of a composition described herein.

Additional embodiments are methods for affecting the proteasome-dependent regulation of oncoproteins and methods of treating or inhibiting cancer growth, each method including exposing a cell (in vivo, e.g., in a subject, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a composition disclosed herein.

In another embodiment, the disclosed compositions are useful for the treatment of a parasitic infection, such as infections caused by protozoan parasites. The proteasome of these parasites is considered to be involved primarily in cell differentiation and replication activities (Paugam, et al. (2003) Trends Parasitol. 19(2):55-59). Furthermore, entamoeba species have been shown to lose encystation capacity when exposed to proteasome inhibitors (Gonzales, et al. (1997) *Arch. Med. Res.* 28, Spec No:139-140). In certain embodiments, the disclosed compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed compositions are useful for the treatment of parasitic infections in animals and livestock caused by a protozoan parasite selected from *Plasmodiumhermani, Cryptosporidium* sps., *Echinococcusgranulosus, Eimeria tenella*, and *Sarcocystis neurona*. Other proteasome inhibitors for co-treatment of parasitic diseases with the inhibitors herein are described in WO 98/10779.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Furthermore, the disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the β2/β2i subunit and inhibiting the proteolytic activities associated therewith. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

The invention is described in greater detail by the following non-limiting examples.

Example 1

Synthesis of Inhibitors

The synthesis of Boc-Arg(Pbf)-ek is shown in Scheme (Pbf, 2,2,4,6,7-pentamethyldihydrobenzofuran-5-sulfonyl; boc, tert-butoxycarbonyl).

SCHEME 1

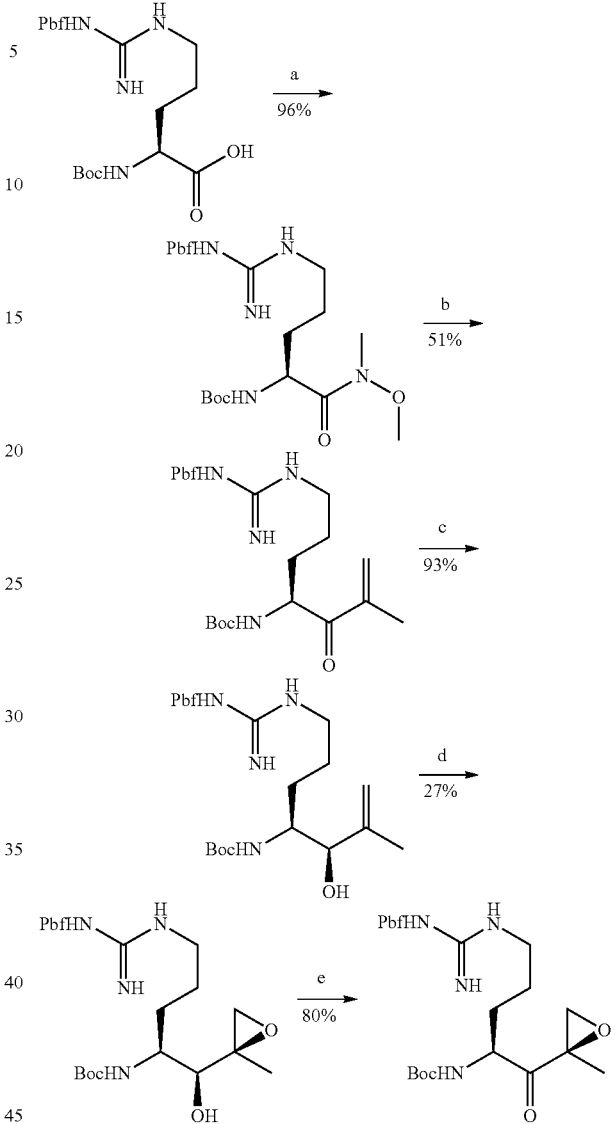

Reagents and Conditions of Scheme 1:
(a) $CH_3NH(OCH_3)$—HCl, HBTU (0-(benzotriazol-1-yl)-N,N,N',N'-tetramethyluronium hexafluorophosphate), DIPEA (diisopropyethylamine), $CH_2Cl_2$, room temperature; (b) 2-Bromopropene/t-BuLi, THF, −78° C.; (c) $NaBH_4$, $CeCl_3$-$7H_2O$, methanol, 0° C.; (d) t-BuOOH, $VO(acac)_2$, $CH_2Cl_2$, 0° C. to room temperature (acac, acetyacetonate); (e) Dess-Martin periodinane, DMSO, 0° C. to room temperature.

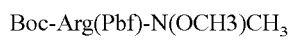

Diisopropylethylamine (5.3 mL, 30.4 mmol) was added to a suspension of Boc-Arg(Pbf)-OH (2 g, 3.8 mmol), N,O-dimethylhydroxylamine hydrochloride (2.23 g, 22.8 mmol) and HBTU (1.58 g, 4.18 mmol) in dichloromethane (10 mL). The resulting solution was stirred at room temperature overnight, diluted with dichloromethane, washed successively with 1N HCl, aq. $NaHCO_3$, brine, dried over $Na_2SO_4$ and concentrated. The crude product was purified by column chromatography (EtOAc, SiO$_2$) to yield 2.07 g (96%) of Boc-Arg(Pbf)-NMe(OMe). $^1$H NMR (CDCl$_3$) δ 1.42 (s, 9H), 1.46 (s, 6H), 1.54-1.76 (m, 4H), 2.09 (s, 3H), 2.53 (s, 3H), 2.59 (s, 3H), 2.96 (s, 2H), 3.10-3.20 (m, 1H), 3.20 (s, 3H), 3.32-3.44 (m, 1H), 3.74 (s, 3H), 4.60-4.70 (m, 1H), 5.49 (br d, 1H, J=8.7 Hz), 6.12 (br s, 2H), 6.32 (br s, 1H). $^{13}$C NMR (CDCl$_3$) δ 12.6, 12.7, 14.4, 19.3, 19.6, 25.2, 28.3, 28.4, 28.6, 28.7, 28.9, 41.0, 43.4, 60.6, 80.2, 86.5, 117.6, 124.7, 132.4, 133.2, 138.5, 156.3, 156.4, 158.8.

Boc-Arg(Pbf)-C(CH$_3$)=CH$_2$ 1.2M tert-Butyllithium solution in pentane (28.4 mL, 34.13 mmol) was added drop-wise to a solution of 2-bromopropene (1.52 mL, 17.5 mmol) in THF (35 mL) at −78° C. under inert atmosphere. Upon addition, the reaction mixture was stirred for an additional 30 minutes, then transferred drop-wise via canula into a stirred solution of Boc-Arg(Pbf)-NMe(OMe) (1 g, 1.75 mmol) in THF (35 mL) at −78° C. The resulting solution was stirred for another 3 hours at −78° C., after which saturated aq. NH$_4$Cl was added, the mixture was allowed to warm up to room temperature with stirring and extracted with EtOAc. The combined organic extracts were washed with brine, dried over Na$_2$SO$_4$ and concentrated. Column chromatography (1:3 hexanes-EtOAc) afforded 0.49 g (51%) of the target ketone Boc-Arg(Pbf)-C(CH$_3$)=CH$_2$. $^1$H NMR (CDCl$_3$) δ 1.42 (s, 9H), 1.47 (s, 6H), 1.57-1.70 (m, 3H), 1.71-1.78 (m, 1H), 1.89 (s, 3H), 2.10 (s, 3H), 2.52 (s, 3H), 2.58 (s, 3H), 2.96 (s, 2H), 3.10-3.20 (m, 1H), 3.40-3.50 (m, 1H), 5.01 (br t, 1H, J=8.0 Hz), 5.55 (br d, 1H, J=8.0 Hz), 5.91 (s, 1H), 5.98 (s, 1H), 6.14 (br s, 2H), 6.33 (br s, 1H). $^{13}$C NMR (CDCl$_3$) δ 12.2, 13.9, 17.7, 19.1, 25.1, 31.1, 40.5, 43.0, 53.4, 79.6, 86.2, 117.2, 124.4, 126.4, 131.9, 132.8, 138.0, 141.8, 155.6, 156.2, 158.5, 200.4 (two signals missing due to overlap).

1-(2-Propenyl)-αN-Boc,ωN-Pbf-argininol

Sodium borohydride (48 mg, 1.25 mmol) was added in portions to a stirred solution of Boc-Arg(Pbf)-C(CH$_3$)=CH$_2$ (0.49 g, 0.89 mmol) and cerium(III) chloride heptahydrate (0.5 g, 1.34 mmol) in methanol (10 mL) at 0° C. The reaction mixture was stirred for an additional 30 minutes at 0° C., quenched with several drops of acetic acid for 15 minutes and concentrated. The residue was partitioned between water and EtOAc, aq. layer extracted with additional portions of EtOAc. The combined organic extracts were washed with brine, dried over Na$_2$SO$_4$ and concentrated to afford 0.46 g (93%) of the target allylic alcohol. $^1$H NMR(CDCl$_3$) δ 1.42 (s, 9H), 1.45 (s, 6H), 1.45-1.66 (m, 4H), 1.70 (s, 3H), 2.09 (s, 3H), 2.51 (s, 3H), 2.57 (s, 3H), 2.95 (s, 2H), 3.00-3.16 (m, 1H), 3.26-3.40 (m, 1H), 3.65-3.80 (m, 1H), 4.08 (br s, 1H), 4.91-5.07 (m, 1H), 4.95 (s, 1H), 5.01 (s, 1H), 6.11 (br s, 2H), 6.26 (br s, 1H). $^{13}$C NMR(CDCl$_3$) δ 11.7, 12.3, 17.7, 18.8, 19.2, 25.7, 41.0, 43.1, 77.4, 79.3, 86.2, 112.0, 117.3, 124.5, 132.1, 132.7, 138.2, 144.5, 156.2, 158.6 (four signals missing due to overlap).

1-(2-Methyloxiranyl)-αN-Boc,ωN-Pbf-argininol

Vanadyl acetylacetonate (20 mg, 0.075 mmol) was dissolved in a solution of 1-(2-propenyl)-αN-Boc,ωN-Pbf-argininol (0.46 g, 0.83 mmol) in dichloromethane (15 mL) at 0° C. 5M tert-Butyl hydroperoxide solution in decane (0.33 mL) was then added at 0° C., cooling was removed, the reaction mixture stirred at room temperature for 15 minutes and quenched with saturated aq. NaHCO$_3$. The aq. layer was further extracted with dichloromethane, the combined organic extracts were washed with brine, dried over Na$_2$SO$_4$ and concentrated. The residue was separated by column chromatography (1:4 hexanes-EtOAc to 100% EtOAc) to afford 53 mg (12%) of unreacted starting material and 0.13 g (27%) of the target epoxyalcohol. $^1$H NMR (CDCl$_3$) δ 1.31 (s, 3H), 1.40-1.50 (m, 3H), 1.41 (s, 9H), 1.46 (s, 6H), 1.56-1.64 (m, 1H), 2.08 (s, 3H), 2.49 (s, 3H), 2.56 (s, 3H), 2.59 (d, 1H, J=4.5 Hz), 2.88 (d, 1H, J=5.0 Hz), 2.95 (s, 2H), 3.10-3.20 (m, 1H), 3.20-3.30 (m, 1H), 3.65 (br m, 1H), 3.76 (br m, 1H), 5.25 (d, 1H, J=4.5 Hz), 6.26-6.35 (br m, 3H). $^{13}$C NMR (CDCl$_3$) δ 12.68, 18.11, 18.31, 19.36, 19.57, 28.32, 28.52, 28.71, 28.91, 43.46, 57.51, 60.62, 74.27, 80.24, 86.56, 117.67, 124.78, 132.52, 133.18, 138.59, 156.39, 156.78, 158.91 (one signal missing due to overlap.

Boc-Arg(Pbf)-ek

Dess-Martin periodinane (0.23 g, 0.54 mmol) was added to a stirred half-frozen solution of 1-(2-methyloxiranyl)-αN-Boc,ωN-Pbf-argininol (0.13 g, 0.24 mmol) in DMSO (4 mL) at 0° C. The reaction mixture was allowed to warm up to room temperature and stirred overnight, then cooled and quenched with saturated aq. NaHCO$_3$. The resulting aq. solution was extracted with EtOAc, organic extracts were washed with brine, dried over Na$_2$SO$_4$ and concentrated. Column chromatography (EtOAc) afforded 0.11 g (80%) of the target epoxyketone. $^1$H NMR (CDCl$_3$) δ 1.40 (s, 9H), 1.46 (s, 6H), 1.50 (s, 3H), 1.54-1.68 (m, 3H), 1.72-1.82 (m, 1H), 2.10 (s, 3H), 2.52 (s, 3H), 2.58 (s, 3H), 2.89 (d, 1H, J=4.8 Hz), 2.96 (s, 2H), 3.14 (d, 1H, J=4.2 Hz), 3.15-3.25 (m, 1H), 3.30-3.40 (m, 1H), 4.25 (br t, 1H, J=8.4 Hz), 5.31 (d, 1H, J=8.7 Hz), 6.20-6.45 (br s, 3H). $^{13}$C NMR (CDCl$_3$) δ 12.4, 16.6, 17.9, 19.3, 25.5, 28.3, 28.6, 40.6, 43.2, 52.3, 58.9, 80.0, 86.3, 117.4, 124.5, 129.5, 132.2, 132.8, 138.3, 155.9, 156.2, 158.7, 213.4. HRMS (ESI, m/z): calculated for [M+H]$^+$ (C$_{27}$H$_{43}$N$_4$O$_7$S) 567.2847. Found 567.2841.

General Procedure for the Synthesis of Active Peptides

The left-hand dipeptides were synthesized by conventional techniques on solid phase. A mixture of Boc-Arg(Pbf)-ek (10 mg, 0.018 mmol) and toluene (ca. 2 mL) was concentrated in vacuo and the Boc group was removed by stirring the residue in 16% TFA (trifluoroacetic acid) in dichloromethane for 30 minutes at room temperature. The reaction mixture was concentrated in vacuo and dried by azeotropic evaporation of toluene. To the solid residue was added a solution of the appropriate left-hand dipeptide (1.1-2 equiv) and HBTU (1.3-2 equiv) in DMF (2 mL). Diisopropylethylamine (4-5 equiv) was then added, the reaction mixture was stirred at room temperature overnight and concentrated in vacuo. The crude protected peptide was isolated by column chromatography (EtOAc), further purified by RP HPLC (0.06% TFA in water—acetonitrile gradient). The remaining protective groups were removed by stirring in 50% TFA in dichloromethane for 2 hours at room temperature. Upon concentration in vacuo, the residue was triturated with water, filtered through a syringe filter and the filtrate was lyophilized to afford the target active peptide (as a TFA salt), the identity of which was confirmed by $^1$H NMR and HRMS.

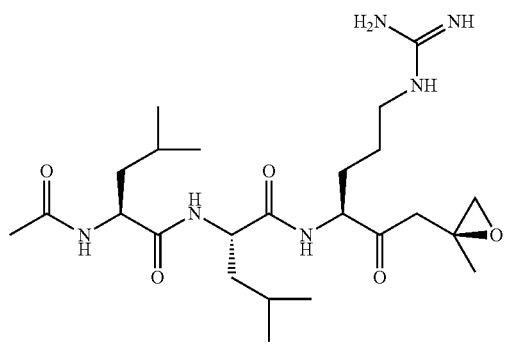 [SMILES: CC(=O)N[C@@H](CC(C)C)C(=O)N[C@@H](CC(C)C)C(=O)N[C@@H](CCCNC(=N)N)C(=O)C[C@@]1(C)CO1]

NC-002

Ac-Leu-Leu-Arg-ek was prepared from Ac-Leu-Leu-OH and Boc-Arg(Pbf)-ek. $^1$H NMR (CD$_3$OD) δ 0.91 (br s, 6H), 0.96 (br s, 6H), 1.30-1.90 (m, 12H), 1.46 (s, 3H), 1.97 (s, 3H), 2.95 (d, 1H, J=5.0 Hz), 3.14-3.25 (m, 2H), 4.30-4.40 (m, 2H), 4.40-4.50 (m, 1H), 8.06 (d, 1H, J=8.0 Hz), 8.15 (d, 1H, J=8.0 Hz), 8.42-8.47 (br m, 1H). HRMS (ESI, m/z): calculated for [M+H]$^+$ (C$_{23}$H$_{43}$N$_6$O$_5$) 483.3289. Found 483.3285.

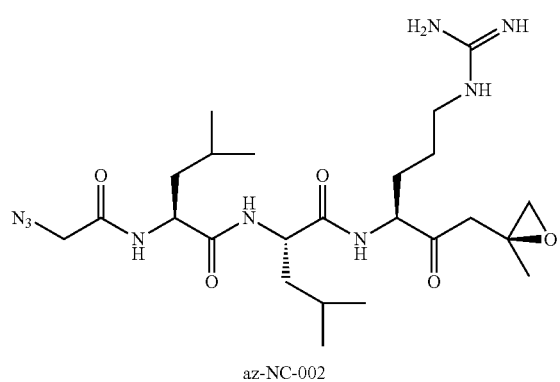 [SMILES: CC(C)C[C@H](NC(=O)CN=[N+]=[N-])C(=O)N[C@@H](CC(C)C)C(=O)N[C@@H](CCCNC(=N)N)C(=O)C[C@@]1(C)CO1]

az-NC-002

Az-Gly-Leu-Leu-Arg-ek (SEQ ID NO:3) was prepared from az-Gly-Leu-Leu-OH and Boc-Arg(Pbf)-ek. $^1$H NMR (CD$_3$OD) δ 0.90-1.00 (m, 12H), 1.34-1.38 (m, 6H), 1.47 (s, 3H), 1.49-1.72 (m, 6H), 2.95 (d, 1H, J=5.0 Hz), 3.17-3.22 (m, 1H), 3.22 (d, 1H, J=5.5 Hz), 3.92 (s, 2H), 4.32-4.40 (m, 2H), 4.47 (dd, 1H, J=10.0, 3.5 Hz), 8.14 (d, 1H, J=8.0 Hz), 8.18 (d, 1H, J=8.0 Hz), 8.50-8.55 (m, 1H). HRMS (ESI, m/z): calculated for [M+H]$^+$ (C$_{23}$H$_{42}$N$_9$O$_5$) 524.3303. Found 524.3299.

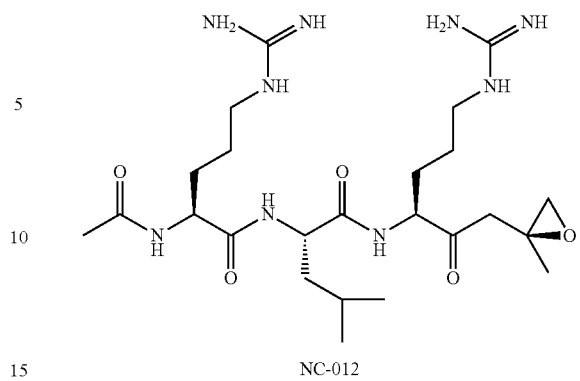

NC-012

Ac-Arg-Leu-Arg-ek was prepared from Ac-Arg(Pbf)-Leu-OH and Boc-Arg(Pbf)-ek. $^1$H NMR (CD$_3$OD) δ 0.86-1.00 (m, 6H), 1.46 (s, 3H), 1.52-1.90 (m, 11H), 2.01 (s, 3H), 2.92 (d, 1H, J=5.0 Hz), 3.12-3.26 (m, 4H), 3.19 (d, 1H, J=5.0 Hz), 4.30-4.40 (m, 2H), 4.44-4.47 (m, 1H). HRMS (ESI, m/z): calculated for [M+H]$^+$ (C$_{23}$H$_{44}$N$_9$O$_5$) 526.3460. Found 526.3458.

NC-022

HMB-Val-Ser-Arg-ek was prepared from HMB-Val-Ser(OtBu)—OH and Boc-Arg(Pbf)-ek. $^1$H NMR (CDCl$_3$) δ 1.01 (d, 3H, J=7.0 Hz), 1.04 (d, 3H, J=7.0 Hz). 1.34-1.40 (m, 1H), 1.47 (s, 3H), 1.46-1.55 (m, 1H), 1.58-1.68 (m, 2H), 1.82-1.91 (m, 1H), 2.10-2.19 (m, 1H), 2.20 (s, 3H), 2.95 (d, 1H, J=5.5 Hz), 3.12-3.20 (m, 2H), 3.23 (d, 1H, J=5.0 Hz), 3.76-3.80 (m, 2H), 4.32-4.35 (m, 1H), 4.44 (t, 1H, J=5.5 Hz), 4.56 (dd, 1H, J=10.0, 4.5 Hz), 6.82-6.85 (m, 2H), 7.05 (t, 1H, J=8.0 Hz). HRMS (ESI, m/z): calculated for [M+H]$^+$ (C$_{25}$H$_{39}$N$_9$O$_7$) 535.2875. Found 535.2872.

Example 2

Assays and Cell Culture

Proteasome Purification and Assays.

26S proteasomes were purified from rabbit muscle using known methods (Screen, et al. (2010) supra). To determine inhibition of purified proteasomes, proteasomes were incubated with inhibitors for 30 minutes at 37° C. followed by assay of activity with fluorogenic substrates Suc-LLVY-amc (SEQ ID NO:8; chymotrypsin-like site), Ac-RLR-amc (trypsin-like site), and Ac-nLPnLD-amc (SEQ ID NO:9; caspase-like site) according to established methods (Geurink, et al. (2010) *J. Med. Chem.* 53:2319-23).NOVEX Bis-Tris gels (12%, Invitrogen) with MOPS running buffer were used for electrophoretic separation of catalytic subunits modified by active-site probes. Inhibition of active sites inside cells was assayed using luminescent PROTEASOMEGLO assay (Promega; Moravec, et al. (2009) *Anal. Biochem.* 387:294-302) according to known methods (Britton, et al. (2009) _supra). Cathepsin B, H, L, S activity was measured with pan-cathepsin substrate Z-FR-amc (Kirschke & Wiederanders (1994) *Methods Enzymol.* 244:500-11) in extracts of cytosol-less cells at pH 6.0 (Screen, et al. (2010) supra). Cathepsin D activity was measured in cytosol-less extracts using SENSOLYTE520 Cathepsin D Fluorometric Assay Kit (AnaSpec). Combined cathepsin D and E activity was measured using the same kit, in which cathepsin D substrate provided with the kit was replaced with 7-Methoxycoumarin-GKPILFFRLK(Dnp)-X'—NH$_2$ (SEQ ID NO:10; where "X'" stand for D-Arg) internally quenched fluorogenic substrate of cathepsin D and E. In this case, pH 3.0 assay buffer used for cell extraction. All activity observed using both procedures was inhibited by more than 98% by specific inhibitor of aspartic proteases pepstatin A.

Cell Culture.

All cells were cultured in RPMI-1640 supplemented with 10% fetal bovine serum. Viability of multiple myeloma cells was measured with ALAMAR BLUE mitochondrial dye conversion assay. Viability of peripheral blood mononuclear cells (PBMNCs) was measured using CELL TITER-GLO luminescent cell viability assay (Promega), which is based on quantification of ATP present in the cells. Caspase-3/7 activity was measured using APO-ONE 3/7 homogeneous assay (Promega). (This assay uses Ac-DEVD-Rhodamine-110 (SEQ ID NO:11) cell-permeable fluorogenic substrate.)

Inhibitors used in the assays included Bortezomib, which was purchased from LC laboratories, and Carfilzomib, which was synthesized using established methods (Demo, et al. (2007) supra; Zhou, et al. (2009) supra; Britton, et al. (2009) supra).

Isolation and Identification of Polypeptides Modified by az-NC-002.

Cells were treated with the activity-based site probe overnight and lysed with 50 mM Tris-HCl, 10% glycerol, 5 mM MgCl$_2$, 0.5 mM EDTA, 0.5% CHAPS, 1 mM ATP. After 1 hour treatment with 100 µM BioP (Verdoes, et al. (2008) *Chembiochem.* 9:1735-8), proteins were denatured with 1% SDS, followed by affinity purification of biotinylated polypeptides on streptavidin-coated magnetic beads. After on-beads trypsin digestion, samples were analyzed by LC-MS/MS (Florea, et al. (2010) *Chem. Biol.* 17:795-801). IRDYE800 CW-conjugated streptavidin was purchased from Rockland, hsc71 antibodies from Abcam (Cat #19136), and P2 antibodies from Abgent (Cat #AP2914b).

Example 3

Design and Characterization of Inhibitors

Peptide epoxyketones were designed to target the trypsin-like site. Peptide epoxyketones are the most specific of the several structural classes of proteasome inhibitors (Kisselev & Goldberg (2001) supra; Groll & Huber (2004) supra; Kisselev (2008) *Chem. Biol.* 15:419-21). By forming a stable morpholino adduct with the proteasome catalytic N-terminal threonine, the inhibitors take specific advantage of the proteasome's unique mechanism for cleaving peptide bonds (Groll, et al. (2000) *J. Am. Chem. Soc.* 122:1237-1238). In more than a decade of research since the discovery of this class of proteasome inhibitors (Meng, et al. (1999) *Proc. Natl. Acad. Sci. USA* 96:10403-10408), no off-target effects of epoxyketones have been found.

Using conventional nomenclature (Britton, et al. (2009) supra), the inhibitors of trypsin-like sites disclosed herein are designated as NC-0X2, where "NC" stands for the Norris Cotton Cancer Center, "2" indicates that the compound inhibits β2 and/or β2i sites, and "X" indicates a variable character. The first compound, NC-002 (Ac-LLR-ek), is the epoxyketone derivative of leupeptin. Leupeptin (Ac-Leu-Leu-Arg-al) is a cell-permeable inhibitor of cysteine proteases. In the context of purified proteasome, this peptide aldehyde is a specific inhibitor of the trypsin-like sites (Kisselev, et al. (2006) supra; McCormack, et al. (1998) *Biochemistry* 37:7792-7800). Peptide aldehydes inhibit serine, cysteine, and threonine proteases. It was reasoned that replacing the aldehyde in leupeptin with a highly proteasome-specific epoxyketone (Groll, et al. (2000) supra) to generate Ac-LLR-amc (NC-002) would eliminate reactivity with lysosomal cysteine proteases, retain specificity to the trypsin-like sites, and not alter cell-permeability of the compound. The design of the second compound, NC-012 (Ac-RLR-ek), is based on the sequence of the best substrate of the trypsin-like site (Ac-RLR-amc; Kisselev & Goldberg (2005) *Methods Enzymol.* 398:364-378). The third inhibitor, NC-022 (Hmb-VSR-ek) has the same left-handed peptide fragment as the peptide vinyl-ester inhibitor of the trypsin-like sites reported in the literature (Marastoni, et al. (2005) supra) that has been shown to lack inhibitory activity (Screen, et al. (2010) supra). This fragment was selected because it was optimized to improve specificity towards these sites.

To enable the synthesis of the epoxyketone derivatives of arginine, the established procedure for the synthesis of leucine epoxyketones (Zhou, et al. (2009) supra) was modified to allow for proper protection of the guanidine functional group during the procedure.

The proteasome inhibitory potential of NC-002, NC-012, and NC-022 was initially determined on purified 26S proteasomes from rabbit muscles. All three compounds were potent and specific inhibitors of the trypsin-like sites. NC-012 was the most potent and specific in the series.

NCI-H929 multiple myeloma (MM) cells were subsequently treated overnight with NC-002, NC-012, and NC-022 and their proteasome inhibition profile was determined. NC-002 and NC-022 specifically inhibited trypsin-like activity at sub-micromolar concentrations, but much higher concentrations of NC-012, the most potent inhibitor of the purified enzyme, were required to achieve inhibition in live cells. This decrease in potency with live cells was attributed to poor cell permeability. For cell-permeable compounds, maximal inhibitory effect was achieved within 6-10 hours after addition of NC-022 or NC-002. Importantly, NC-002, the epoxyketone derivative of the cysteine protease inhibitor leupeptin, did not inhibit lysosomal cysteine proteases.

Multiple myeloma cells express constitutive proteasomes and immunoproteasomes, and substrates used for the measurement of activity were cleaved by both. To determine whether there were any differences in inhibition of constitutive proteasomes or immunoproteasomes by NC-002, NC-012, and NC-022, the fluorescent activity-based probe MV-151 (Verdoes, et al. (2006) *Chem. Biol.* 13:1217-1226) was used in a label-competition experiment. Extracts of RPMI-8226 MM cells (which express more immunoproteasomes than NCI-H929 cells) were treated first with the NC inhibitors and then with the MV-151 probe. This was followed by fractionation on SDS-PAGE to separate proteasome subunits and imaging to reveal those subunits labeled by the probe (i.e., unmodified by the inhibitors). All three inhibitors blocked modification of β2 and β2i sites by the probe to a similar extent. Thus, it was concluded that NC-002, NC-012, and NC-022 were equipotent inhibitors of the trypsin-like sites of constitutive and immunoproteasomes.

Example 4

Inhibitors of Trypsin-Like Sites Sensitize Cells to Inhibitors of Chymotrypsin-Like Sites NC-002, NC-012 and NC-022 were also used to characterize trypsin-likes sites as targets and co-targets of anti-neoplastic agents. For this purpose, NC-022 was used as it was the most potent cell-permeable inhibitor. First, it was determined whether selective inhibition of trypsin-like sites was sufficient to reduce cell viability. NCI-H929 cells were treated with NC-022 for 48 hours and cell viability was assayed with ALAMAR BLUE mitochondrial conversion dye. No loss of viability was detected even at concentrations that completely inhibited the trypsin-like sites. Thus, targeting trypsin-like sites was not sufficient to induce cytotoxicity in multiple-myeloma cells. It should be noted that NCI-H929 is the most sensitive to proteasome inhibitors among myeloma cell lines (Britton, et al. (2009) supra).

It was subsequently determined whether NC-022 sensitizes myeloma cells to inhibitors of the chymotrypsin-like sites. Several peptide epoxyketone inhibitors of the chymotrypsin-like sites have been developed (Britton, et al. (2009) supra; Geurink, et al. (2010) supra) and the most specific of these, a pentafluorophenylalanine-containing compound referred to as LU-005 (Geurink, et al. (2010) supra), was used in the experiments herein.

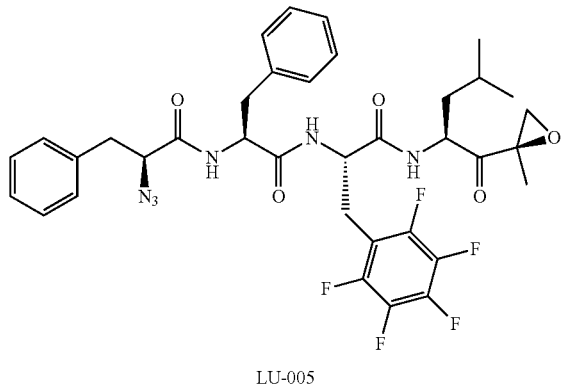 [SMILES: CC(C)C[C@H](NC(=O)[C@H](Cc1c(F)c(F)c(F)c(F)c1F)NC(=O)[C@H](Cc1ccccc1)NC(=O)[C@H](Cc1ccccc1)N=[N+]=[N-])C(=O)[C@@]1(C)CO1]

LU-005

In the first experiment, it was determined whether NC-022 sensitizes cells to LU-005, and what concentrations are needed to achieve this sensitization. Consistent with conventional treatment conditions (Britton, et al. (2009) supra), where it was demonstrated that a specific inhibitor of the caspase-like sites sensitizes myeloma cells to NC-005 (a specific inhibitor of chymotrypsin-like sites; Britton, et al. (2009) supra), cells were treated with LU-005 for 1 hour and then incubated in the presence of different concentrations of NC-022 for 48 hours, whereupon an ALAMAR BLUE assay for cell viability was performed. Dramatic dose-dependent sensitization was observed, with the $IC_{50}$ of LU-005 increasing up to 8.5-fold. This maximal sensitization was achieved at 3 μM NC-022, which caused 90% inhibition of the trypsin-like sites within 4-6 hours after addition of NC-022. NC-002 caused similar sensitization to NC-005. Thus, near-complete inhibition of the trypsin-like sites was needed to achieve maximal sensitization effect.

Example 5

Development of β2-Specific Activity-Based Probe

To further confirm that NC-002, NC-012 and NC-022 were specific for the trypsin-like sites and that the biological activity was not due to off-target effects, az-NC-002 was synthesized as an NC-002-derived, activity-based probe. NC-002 over NC-022 was selected for derivatization because it was easier to introduce an azido group into this molecule. Addition of the azido group did not alter the specificity of the inhibitor. Polypeptides modified by this probe were visualized on western blot after treating extracts of probe-treated NCI-H929 cells with azido-reactive biotinylated phosphane (BioP) in a Staudinger-Bertozzi ligation (Ovaa, et al. (2003) *Angew Chem. Int. Ed. Engl.* 42:3626-3629). One major az-NC-002-specific streptavidin-reactive band was detected. This matched the size of the band of the β2 subunit, which harbors the catalytic threonines of the trypsin-like sites. A weaker band of slightly lower mobility, matching the mobility of β2i band, was also detected. Corroborating that these bands were of proteasomal subunits, az-NC-002 treatment prevented subsequent modification of β2 and β2i subunits by another proteasome-specific probe (Ada-K(Bio)-Ahx$_3$L$_3$VS). A number of endogenously biotinylated proteins in the 70-100 kDa region were also detected and can serve as a loading control.

To further confirm that the probe covalently modified β2 and β2i subunits, proteasome was denatured after BioP modification, biotinylated polypeptides were isolated on streptavidin beads, and bound polypeptides were identified by mass-spectrometry after on-beads trypsin digestion. Peptides derived from β2 and β2i subunits were present in the samples isolated from extracts of the probe-treated cells but not from extracts of the control cells. No peptides derived from other catalytic subunits were detected. Thus, it was concluded that az-NC-002 was a trypsin-like site-specific activity-based probe.

Unexpectedly, several other polypeptides were also reproducibly identified as specific az-NC-002 targets. These include the aspartic protease cathepsin D (29 kDa), molecular chaperone hsc71 (71 kDa), and thioredoxin domain-containing protein TXNDC5 (48 kDa). Of these, lysosomal aspartic protease cathepsin D (Benes, et al. (2008) *Crit. Rev. Oncol. Hematol.* 68:12-28) was of greatest concern. It has the same molecular weight as the β2 subunit, so some of the streptavidin-reactive material in the β2-band may have been cathepsin D. To determine the significance of this potential off-target effect, inhibition of cathepsin D was measured by az-NC-002; however no significant inhibition could be detected. It was concluded that this probe either reacts with cathepsin D outside of the active site or inhibits a small fraction of the enzyme, detectable in the mass-spectrometry experiment but not in the activity assay. Similarly, NC-022 did not inhibit cathepsin D even at concentrations as high as 27 μM. Thus, chemical modification of cathepsin D is unlikely to contribute to the biological effects of the NC compounds.

There were no major streptavidin-reactive az-NC-002-specific bands in the 45-50 kDa and ~70 kDa region of the gel, where two other targets of az-NC-002, TXNDC5 and hsc71, migrate. Probe modification of these proteins was responsible for one of the background bands. Western blot analysis was used to determine which fraction of cellular hsc71 binds to streptavidin beads in extracts of az-NC-002-treated cells. Under conditions when most of β2-antibody reactive material was detected in streptavidin-bound fraction, the majority of hsc71-antibody reactive material was detected in the streptavidin-unbound fractions. Thus, az-NC-022 modifies a small fraction of hsc71 and is therefore very unlikely to affect the overall protein-folding capacity of the cell.

Example 6

NC-022 as a Potent Sensitizer of Myeloma Cells to LU-005

It was also determined whether NC-022 sensitizes other MM cells to LU-005 and whether it is a more potent sensitizer than a specific inhibitor of caspase-like sites NC-001 (Britton, et al. (2009) supra). In a parallel set of experiments, it was tested whether co-inhibiting caspase-like and trypsin-like sites suffices to induce cytotoxicity in the absence of inhibition of the chymotrypsin-like sites and whether such dual inhibition is a stronger sensitizer to LU-005 than inhibition of the trypsin-like sites alone. Four additional myeloma cell lines, MM1.R, RPMI-8226, KMS-18, and KMS-12-BM, were selected for these experiments. These cell lines vary up to 40-fold in their sensitivity to bortezomib and NC-005 (Britton, et al. (2009) supra). In all experiments, NC-022 was used at a concentration that inhibited trypsin-like activity by more than 90% after a 6-hour incubation.

In all MM cell lines, NC-022 reduced the $IC_{50}$ for LU-005 by 4-10-fold. In three (MM1.R, RPMI-8226, KMS-18), NC-022 caused similar sensitization as NC-001. In two others (NCI-H929 and KMS-12-BM), NC-022 was a more potent sensitizer than NC-001. Thus, the trypsin-like sites are important co-targets of anti-neoplastic drugs in multiple myeloma cells; in fact, they are better co-targets than the caspase-like sites.

To confirm that LU-005 functioned as a specific inhibitor of the chymotrypsin-like sites and to determine whether sensitization occurred upon clinically achievable inhibition of the chymotrypsin-like sites, inhibition of all sites was measured at the end of 1 hour treatment with LU-005 (Table 2). In patients treated with bortezomib, inhibition of the chymotrypsin-like sites that can be achieved at maximal tolerated doses does not exceed 70% (Hamilton, et al. (2005) *J. Clin. Oncol.* 23:6107-16); in patients treated with carfilzomib, it approaches 90% (O'Connor, et al. (2009) supra). As can be seen from Table 2, in all but the KMS-18 cell line, sensitization by NC-022 was observed upon clinically achievable 50-80% inhibition of the chymotrypsin-like sites. Thus, sensitization of myeloma cells to specific inhibitors of the chymotrypsin-like sites by NC-022 is of potential clinical significance.

TABLE 2

| Cell line | LU-005 (μm) | Viability (% control) | | +NC-002 & NC-001 | Inhibition of active sites (% control) | | |
|---|---|---|---|---|---|---|---|
| | | −NC-022 | +NC-022 | | β5 | β2 | β1 |
| NCI-H929 | 0.11 | 30 ± 2 | 2 ± 1 | 0.65 ± 0.25 | 86 ± 3 | 11 ± 4 | 6 ± 8 |
| | 0.043 | 80 ± 8 | 10 ± 2 | 1.5 ± 0.5 | 72 ± 8 | 6 ± 4 | 15 ± 20 |
| | 0.011 | 94 ± 11 | 48 ± 3 | 10 ± 4 | 48 ± 5 | −6 ± 1 | 5.5 ± 4.5 |
| | 0.004 | 100 ± 13 | 69 ± 0 | 36 ± 14 | 22 ± 11 | −13 ± 7 | −7 ± 10 |
| | 0.0014 | 97 ± 9 | 77 ± 2 | 50 ± 17 | 22 ± 4 | −9 ± 2 | −14 ± 15 |
| MM1.R | 0.11 | 47 ± 42 | 1.7 ± 0.2 | 1.2 ± 1.2 | 76 ± 3 | 23 ± 4 | 27 ± 5 |
| | 0.043 | 88 ± 20 | 18.5 ± 5.5 | 2.8 ± 1.5 | 54 ± 12 | 5 ± 11 | 6 ± 12 |
| | 0.011 | 106 ± 4 | 57 ± 10 | 15 ± 9 | 31 ± 10 | 5 ± 1 | 3 = 16 |
| | 0.004 | 102 ± 4 | 66 ± 1 | 26 ± 6 | 17 ± 4 | 6.5 ± 0.5 | 6 ± 8 |
| RPMI-8226 | 1.0 | 10 ± 10 | 6 ± 3 | 1 ± 0 | 82 ± 16 | 22 ± 19 | 37 ± 4 |
| | 0.33 | 94 ± 1 | 31 ± 9 | 4.6 ± 0.7 | 62 ± 32 | 13 ± 11 | 37 ± 15 |
| | 0.11 | 108 ± 4 | 95 ± 2 | 39 ± 5 | 49 ± 30 | 3 ± 5 | 23 ± 2 |
| | 0.037 | 109 ± 2 | 104 ± 5 | 76 ± 3 | 45 ± 26 | 1 ± 17 | 16 ± 7 |
| | 0.012 | 109 ± 1 | 108 ± 4 | 82 ± 11 | 16 ± 8 | −21 ± 4 | −34 ± 5 |
| KMS-12-BM | 1.0 | 27 ± 6 | 1.5 ± 0.1 | 1 ± 0 | 95 ± 2 | 29 ± 7 | 11 ± 16 |
| | 0.33 | 80 ± 9 | 12 ± 2 | 2 ± 0 | 81 ± 3 | 3 ± 18 | 6 ± 12 |
| | 0.11 | 94 ± 16 | 65 ± 2 | 20 ± 4 | 56 ± 9 | 4.7 ± 1.1 | 3 ± 16 |
| | 0.037 | 89 ± 8 | 90 ± 5 | 50 ± 2 | 48 ± 9 | −12 ± 1 | −1 ± 5 |
| | 0.012 | 101 ± 5 | 104 ± 9 | 79 ± 6 | 16 ± 8 | −21 ± 3.5 | −34 ± 5 |
| KMS-18 | 9.0 | 45 ± 8 | 17.5 ± 7.5 | 0.8 ± 0.2 | 97 ± 1 | 62 ± 5 | 42 ± 2 |
| | 3.0 | 72 ± 2 | 24 ± 8 | 1 ± 0.1 | 94 ± 4 | 50 ± 14 | 39 ± 12 |
| | 1.0 | 88 ± 16 | 29 ± 12 | 8 ± 4 | 85 ± 6 | 38 ± 5 | 32 ± 4 |
| | 0.33 | 108 ± 0 | 106 ± 16 | 33 ± 20 | 69 ± 8 | 24 ± 6 | 29 ± 7 |
| | 0.11 | 108 ± 1 | 106 ± 4 | 56 ± 16 | 47 ± 4 | 12 ± 16 | 21 ± 16 |
| | 0.037 | 108 ± 1 | 104 ± 3 | 79 ± 14 | 14 | −13 ± 13 | 0 ± 8 |

Cells were treated with LU-005 for 1 hour, followed by measurement of peptidase activities; a fraction of the cells was cultured in the presence of NC-022, of NC-022 and NC-001, or of none of the inhibitors for 48 hours, whereupon cell viability was measured. Values are averages S.E.M. of two (activity) or three (viability) independent measurements. Negative values indicate activation.

Example 7

Effects of Combined Inhibition of Caspase-Like and Trypsin-Like Sites

Due to the lack of effective, selective, and cell-permeable inhibitors of the trypsin-like sites, the effects of combined inhibition of the trypsin-like and caspase-like sites (in the absence of inhibition of the chymotrypsin-like sites) on growth and viability of mammalian cells could not be studied hitherto. It was observed that continuous exposure to a mixture of NC-022 and NC-001 (at concentrations at which caspase-like and trypsin-like sites are both blocked by more than 90%) reduced cell viability by 20-50%. Proteasome inhibitors block cell proliferation and induce apoptosis. This moderate decrease could be a consequence of inhibition of cell proliferation without cell death. To determine whether apoptosis occurs, caspase activation in the NCI-H929 and MM1.R cell lines was measured. It was found that treatment with a combination of NC-001 and NC-002, in contrast to LU-005 treatment, did not cause any significant increase in caspase activity. Therefore, it was concluded that the moderate decrease in viability in cells co-treated with NC-001 and NC-002 was not due to apoptosis and most likely reflected inhibition of cell proliferation. This is the first example of a biological effect on mammalian cells due to inhibition of the caspase-like and trypsin-like sites in the absence of inhibition of the chymotrypsin-like sites.

The effects of the mixture of NC-001 and NC-022 on MM cells sensitivity to LU-005 were subsequently determined. As in the previous experiments, cells were treated with LU-005 for 1 hour and then cultured with a NC-001/NC-022 mixture after removal of LU-005. The mixture of NC-001 and NC-022 appeared to be a much stronger sensitizer than NC-022 alone. Notably, there was always a concentration of LU-005 at which a mixture of NC-001 and NC-002 caused a dramatic loss of cell viability as compared to the effect of LU-005 as a single agent (i.e., from 80-100% to 10-20%). At this concentration, LU-005 inhibited chymotrypsin-like sites by a clinically achievable 50-85% (Table 2). A mixture also sensitized cells at much lower concentrations of LU-005 (i.e., upon much smaller inhibition of chymotrypsin-like sites, Table 2) than either NC-001 or NC-002 alone.

Example 8

NC-022 Specifically Sensitizes Myeloma Cells to Bortezomib and Carfilzomib

To further strengthen the clinical relevance of data herein, it was determined whether NC-022 sensitizes MM cells to the FDA-approved proteasome inhibitor bortezomib and to carfilzomib, a second-generation peptide epoxyketone proteasome inhibitor undergoing phase II-III clinical trials (Demo, et al. (2007) supra; O'Connor, et al. (2009) supra). Two cell lines were used in these experiments, one of the most bortezomib-sensitive (NCI-H929), and one of the most bortezomib-resistant (KMS-12-BM) cell lines (Britton, et al. (2009) supra). Both cell lines were sensitized to the two agents (Table 3). In NCI-H929 cells, sensitization to both compounds occurred upon clinically achievable proteasome inhibition (Table 4). In KMS-12-BM cells, sensitization to bortezomib, although more dramatic than in NCI-H929 cells, was observed above clinically achievable inhibition of the chymotrypsin-like sites. Sensitization to carfilzomib was observed at clinically achievable levels.

TABLE 3

| Inhibitor | Conc. (nM) | Cell line | Viability (% control) −NC-022 | +NC-022 |
|---|---|---|---|---|
| Bortezomib | 100 | NCI-H929 | 2.9 ± 1.5 | 1.9 ± 1.5 |
| | 33 | | 53 ± 17 | 19 ± 19 |
| | 11 | | 106 ± 2 | 65 ± 1 |
| | 3.7 | | 107 ± 5 | 85 ± 3 |
| | 900 | KMS-12-BM | 14 ± 12 | 3.8 ± 2.5 |
| | 300 | | 66 ± 9 | 14 ± 11 |
| | 100 | | 92 ± 9 | 42 ± 10 |
| | 33.3 | | 98 ± 13 | 72 ± 1 |
| Carfilzomib | 33 | NCI-H929 | 30 ± 11 | 4 ± 2 |
| | 11 | | 78 ± 15 | 14 ± 8 |
| | 3.7 | | 99 ± 9 | 36 ± 15 |
| | 900 | KMS-12-BM | 41 ± 7 | 9 ± 1 |
| | 300 | | 71 ± 2 | 15 ± 1 |
| | 100 | | 83.5 ± 3 | 27 ± 5 |
| | 33 | | 91 ± 3 | 40 ± 3 |
| | 11 | | 95 ± 3 | 69 ± 2 |

*Cells were treated with bortezomib and carfilzomib for 1 hour. NC-022 was added and viability was measured 48 hours after the start of the experiment.

TABLE 4

| | | | Inhibition of active sites (% control) | | | | | |
|---|---|---|---|---|---|---|---|---|
| | | | Chymotrypsin-like sites Time after start of experiment | | | Trypsin-like sites Time after start of experiment | | |
| Inhibitor | Conc. (nM) | Cell line | 1 h* | 6 h −NC-022 | 6 h +NC-022 | 1 h | 6 h −NC-022 | 6 h +NC-022 |
| Bortezomib | 100 | NCI-H929 | 96 ± 2 | 86 ± 1 | 93 ± 2 | 36 ± 17 | 45 ± 2 | 96 ± 1 |
| | 33 | | 89 ± 2 | 85 ± 4 | 48 ± 35 | 26 ± 15 | 31 ± 0 | 94 ± 1 |
| | 11 | | 64 ± 7 | 41 ± 3.5 | 34 ± 29 | 8 ± 11 | 14 ± 2 | 93 ± 2 |
| | 3.7 | | 9 ± 7 | 13 ± 1 | 14 ± 13 | 0 ± 7 | 6 ± 4 | 93 ± 2 |
| | 900 | KMS-12-BM | 93 ± 5 | 84 ± 16 | 88 ± 5 | 28 ± 5 | 26 ± 19 | 93 ± 1 |
| | 300 | | 93 ± 3 | 76 ± 18 | 83 ± 6 | 22 ± 12 | 24 ± 18 | 91 ± 2 |
| | 100 | | 90 ± 6 | 64 ± 23 | 75 ± 6 | 19 ± 3 | 15 ± 11 | 92 ± 1 |
| | 33.3 | | 82 ± 8 | 56 ± 24 | 62 ± 7 | 10 ± 11 | 8 ± 15 | 92 ± 0 |
| Carfilzomib | 33 | NCI-H929 | 75 ± 17 | 95 ± 7 | 71 ± 23 | 17 ± 8 | 46 ± 24 | 94 ± 3 |
| | 11 | | 39 ± 35 | 89 ± 11 | 52 ± 32 | 0 ± 14 | 39 ± 36 | 93 ± 2 |
| | 3.7 | | 14 ± 43 | 65.5 | 41 ± 29 | −7 ± 18 | 3 | 93 ± 3 |
| | 900 | KMS-12-BM | 98 ± 3 | 97 ± 0 | 99 ± 4 | 75 ± 14 | 72 ± 2 | 94 ± 3 |
| | 300 | | 97 ± 3 | 97 ± 1 | 95 ± 4 | 49 ± 18 | 69 ± 2 | 93 ± 2 |
| | 100 | | 95 ± 3 | 97 ± 1 | 90 ± 3 | 18 ± 8 | 62 ± 2 | 94 ± 2 |
| | 33 | | 90 ± 3 | 97 ± 1 | 84 ± 6 | 0 ± 11 | 45 ± 4 | 91 ± 2 |
| | 11 | | 75 ± 6 | 67 ± 17 | 63 ± 13 | −3 ± 10 | 5 ± 25 | 91 ± 2 |

*Cells were treated with bortezomib and carfilzomib for 1 hour, and activity was measured immediately after washout of the drug. NC-022 was added, and 5 hours after NC-022 addition, proteasome activity was measured again. Note that trypsin-like activity was inhibited by >90% but inhibition of the chymotrypsin-like activity was not altered by NC-022 treatment.

To assess whether co-inhibition of trypsin-like sites increases toxicity to normal cells, it was determined whether NC-022 increased toxicity of bortezomib and carfilzomib to PBMNCs. NC-022 did not sensitize cells from any of the three donors to either of two agents. This lack of sensitization was unexpected because NC-001 sensitizes PBMNCs to inhibitors of the chymotrypsin-likes sites (Britton, et al. (2009) supra). Thus, NC-022 selectively sensitizes malignant MM cells to bortezomib and carfilzomib.

Example 9

Synthesis of Additional Epoxyketones and Vinyl Sulfones with 4-Aminomethylene-L-Phenylalanine in the P1 Position This Example describes the development of inhibitors targeting the trypsin-like subunits (β2 and β2i) by modification of the P1 site, which plays a key role in subunit binding, with basic residues. The general structure of these inhibitors is based on the tripeptide vinyl sulfone Z-L$_3$VS 3, which targets all proteasome active sites (Bogyo, et al. (1997) *Proc. Natl. Acad. Sci. USA* 94:6629-6634). The P1 leucine side chain was replaced by a benzyl amine (Scheme 2). In addition to the vinyl sulfone electrophilic trap, the epoxyketone featured by natural proteasome inhibitor epoxomicin was incorporated as well, since it displays a specific reactivity towards proteasome active sites (Kisselev & Goldberg (2001) *Chem. Biol.* 8:739-758; Kim, et al. (1999) *Bioorg. Med. Chem. Lett.* 9:3335-3340). The N-terminal benzyloxycarbonyl group was replaced by the structurally related azidophenylalanine, which opens the possibility for additional modifications (Ovaa, et al. (2003) *Angew. Chem. Int. Ed.* 42:3626-3629; van Swieten, et al. (2005)_Org. Biomol. Chem. 3:20-27; Verdoes, et al. (2009) *Eur. J. Org. Chem.* 3301-3313), yet it does not significantly influence the inhibitory properties compared to the benzyloxycarbonyl group.

many). Traces of water were removed from reagents used in reactions that require anhydrous conditions by co-evaporation with toluene. Solvents that were used in reactions were stored over 4 Å molecular sieves, except methanol and acetonitrile which were stored over 3 Å molecular sieves. Column chromatography was performed on Screening Devices b.v. Silica Gel, with a particle size of 40-63 μm and pore diameter of 60 Å. The eluents toluene, ethyl acetate and petroleum ether (40-60° C. boiling range) were distilled prior to use. TLC analysis was conducted on Merck aluminium sheets (Silica gel 60 F$_{254}$). Compounds were visualized by UV absorption (254 nm), by spraying with a solution of $(NH_4)_6Mo_7O_{24}\cdot 4H_2O$ (25 g/L) and $(NH_4)_4Ce(SO_4)_4\cdot 2H_2O$ (10 g/L) in 10% sulfuric acid, a solution of KMnO$_4$ (20 g/L) and K$_2$CO$_3$ (10 g/L) in water, or ninhydrin (0.75 g/L) and acetic acid (12.5 mL/L) in ethanol, where appropriate, followed by charring at ca. 150° C. $^1$H- and $^{13}$C-NMR spectra were recorded on a Bruker AV-400 (400 MHz) spectrometer. Chemical shifts are given in ppm (δ) relative to tetramethylsilane, CD$_3$OD or CDCl$_3$ as internal standard. High resolution mass spectra were recorded by direct injection (2 μL of a 2 μM solution in water/acetonitrile 50/50 (v/v) and 0.1% formic acid) on a mass spectrometer (Thermo Finnigan LTQ ORBITRAP) equipped with an electrospray ion source in positive mode (source voltage 3.5 kV, sheath gas flow 10, capillary temperature 250° C.) with resolution R=60,000 at m/z 400 (mass range m/z=150-2,000) and dioctylpthalate (m/z=391.28428) as a "lock mass". The high resolution mass spectrometer was calibrated prior to measurements with a calibration mixture (Thermo Finnigan). Optical rotations$_{[\alpha]_D}{}^{23}$ were recorded on a Propol automatic polarimeter. LC-MS analysis was performed on a Finnigan Surveyor HPLC system with a Gemini C18 50×4.60 mm column (detection at 200-600 nm), coupled to a Finnigan LCQ Advantage Max

SCHEME 2

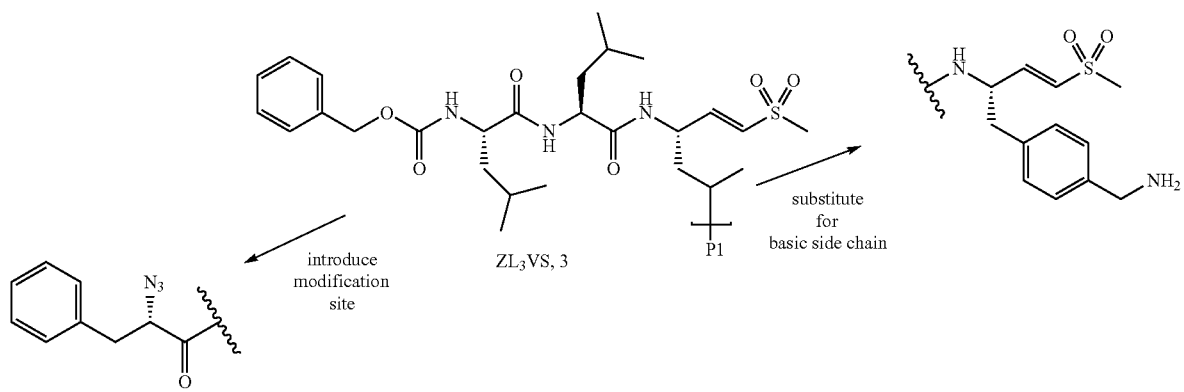

The inhibitors targeting the trypsin-like subunits are shown below.

General Procedures for Synthesis.

Tetrahydrofuran was distilled over LiAlH$_4$ prior to use. Acetonitrile (ACN), dichloromethane (DCM), N,N-dimethylformamide (DMF), methanol (MeOH), diisopropylethylamine (DiPEA) and trifluoroacetic acid (TFA) were of peptide synthesis grade, purchased at Biosolve, and used as received. All general chemicals (Fluka, Acros, Merck, Aldrich, Sigma) were used as received. O-(1H-6-Chlorobenzotriazolyl)-1,1,3,3-tetramethyluronium hexafluorophosphate (HCTU) was purchased at Iris Biotech (Marktrewitz, Germass spectrometer with ESI. The applied buffers were H$_2$O, ACN and 1.0% aq. TFA. HPLC purifications were performed on a Gilson HPLC system coupled to a Phenomenex Gemini 5 μm 250×10 mm column and a GX281 fraction collector. The applied buffers were: 0.1% aq. TFA and ACN.

Procedure I: Azide Coupling of N$_3$Phe-Leu-Leu-NHNH$_2$ or HMB-Val-Ser(tBu)-NHNH to an Amine-Warhead Followed by Acidic Deprotection N$_3$Phe-Leu-Leu-NHNH$_2$ 38 or HMB-Val-Ser(tBu)-NHNH$_2$ (1 eq.) was dissolved in a 9:1 mixture of DCM/DMF (10 mL/mmol) and cooled to −35° C. To this were added tert-butylnitrite (1.1 eq.) and HCl (2.8 eq. as a 4 M solution in 1,4-dioxane) and the mixture was stirred for 3 hours at −35° C. Next, a mixture of the deprotected amine (1.1 eq.) and DiPEA (5 eq.) in DMF (1 mL) were added. The reaction was slowly warmed to room temperature and stirred for another 12 hours before being diluted with DCM and extracted with 1M aq. HCl (2×), saturated aq. $Na_2CO_3$ (2×) and brine. After drying ($MgSO_4$) and concentrating the obtained crude product was dissolved in DCM (2.5 mL/mmol). TFA (2.5 mL/mmol) was added and the mixture was stirred for 30 minutes, after which it was concentrated under reduced pressure in the presence of toluene (3×). The obtained crude product was purified by RP-HPLC.

$N_3$-Phe-Leu-Leu-$NHNH_2$ (38)

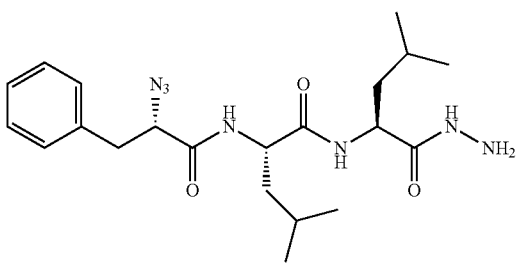 [SMILES: CC(C)C[C@H](NC(=O)[C@H](Cc1ccccc1)N=[N+]=[N-])C(=O)N[C@@H](CC(C)C)C(=O)NN]

This compound was synthesized via general Boc-based peptide coupling procedures using HCTU from H-Leu-OMe, Boc-Leu-H and $N_3$-Phe-H. The last step involved the introduction of the hydrazide by stirring of a mixture containing tripeptide $N_3$-Phe-Leu-Leu-OMe (1.51 g, 3.49 mmol) and hydrazine monohydrate (30 eq., 105 mmol, 5.1 mL) in MeOH (30 mL) for 15 hours at room temperature. Compound 38 was obtained after coevaporation of the mixture with toluene (3×) as a colourless solid (yield: 1.51 g, 3.49 mmol, quant.). LC-MS: $R_t$ (min): 6.87 (ESI-MS (m/z): 432.13 (M+H$^+$)).

(S)-2-((Benzyloxy)carbonyl)amino)-3-(4-((2,2,2-trichloroacetamido)methyl)phenyl)propanoic acid (9)

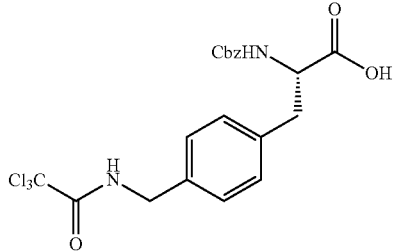

L-Phenylalanine (8, 8.26 g, 50.0 mmol) was added in portions to concentrated $H_2SO_4$ (35 mL) maintaining the temperature at 25° C. N-(hydroxymethyl) trichloroacetamide (1.05 eq., 52.5 mmol, 10.1 g) was added in portions while maintaining the temperature at 20-25° C. The cooling bath was removed and the light-brown cloudy solution was stirred at room temperature for 1 hour. The reaction mixture was added to ice (500 mL) and the pH was adjusted to pH 5.5 with 8 M aq. NaOH solution while maintaining the quench temperature at 15-20° C. The white solid was filtered off and washed with ice-cold $H_2O$. The residue was dissolved in a 1:1 mixture of $H_2O$/dioxane (100 mL) and the pH was adjusted to pH 9 by addition of $Na_2CO_3$. Next, benzyl chloroformate (7.32 mL, 50.0 mmol) was added and the mixture was stirred for 4 hours. Concentrated aq. HCl was added until pH 1 and the mixture was extracted twice with EtOAc. The combined organic layers were extracted with brine, dried ($MgSO_4$) and concentrated under reduced pressure. The resulting crude product was purified by column chromatography (25%→60% EtOAc/PE) and the title compound was obtained as a colourless solid (yield: 8.29 g, 17.5 mmol, 35%). $^1$H NMR (400 MHz, $CDCl_3$): δ=10.16 (s, 1H), 7.31-7.21 (m, 6H), 7.13 (d, J=7.88 Hz, 2H), 7.09 (d, J=7.97 Hz, 2H), 5.58 (d, J=8.21 Hz, 1H), 5.05-4.97 (m, 2H), 4.60 (dd, J=13.68, 6.42 Hz, 1H), 4.40 (d, J=5.54 Hz, 2H), 3.14 (dd, J=13.57, 4.65 Hz, 1H), 3.01 (dd, J=13.81, 6.53 Hz, 1H) ppm. $^{13}$C NMR (100 MHz, $CDCl_3$): δ=174.70, 162.06, 155.85, 135.68, 135.31, 135.15, 129.57, 128.31, 128.28, 127.76, 127.57, 92.30, 66.91, 54.41, 44.54, 36.99 ppm.

(S)-2-(((Benzyloxy)carbonyl)amino)-3-(4-(((tert-butoxycarbonyl)amino)methyl)phenyl)propanoic acid (10)

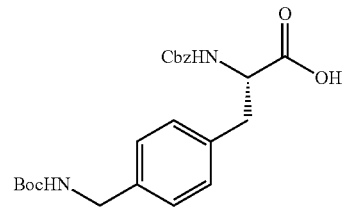 [SMILES: CC(C)(C)OC(=O)NCc1ccc(C[C@H](NC(=O)OCc2ccccc2)C(=O)O)cc1]

Compound 9 (2.82 g, 5.94 mmol) was treated with 20% w/w NaOH in $H_2O$/EtOH (1:1) for 1 hour after which TLC analysis indicated complete conversion of starting material. Next, 3 M aq. HCl was added until pH 7 and the mixture was concentrated under reduced pressure. The resulting crude compound was dissolved in THF (40 mL) and cooled to 0° C. $Boc_2O$ (1.5 eq., 8.91 mmol, 2.0 g) was added and the solution was basified by addition of $Na_2CO_3$ until pH 9. The mixture was stirred at room temperature for 3 hours, after which it was acidified with 10% w/v aq. HCl until pH and extracted with EtOAc (3×). The combined organic layers were extracted with brine, dried over $MgSO_4$ and concentrated under reduced pressure. The resulting crude mixture was purified by column chromatography (20%→100% EtOAc/PE) and the title compound was obtained as a colourless solid (yield: 1.90 g, 4.45 mmol, 75%). $^1$H NMR (400 MHz, $CDCl_3$): δ=9.32 (s, 1H), 7.36-7.28 (m, 5H), 7.16-7.02 (m, 4H), 5.33 (d, J=7.64 Hz, 1H), 5.09 (q, J=12.32, 12.32, 12.29 Hz, 2H), 4.95 (s, 1H), 4.65 (d, J=6.41 Hz, 1H), 4.26-4.19 (m, 2H), 3.20-3.04 (m, 2H), 1.45 (s, 9H) ppm. $^{13}$C NMR (100 MHz, $CDCl_3$):

δ=174.79, 156.16, 155.77, 137.47, 136.15, 134.80, 129.61, 128.46, 128.14, 128.03, 127.69, 79.85, 66.99, 54.52, 44.31, 37.30, 28.36 ppm.

(S)-2-(((Benzyloxy)carbonyl)amino)-3-(4-(((tert-butoxycarbonyl)amino)methyl)phenyl)-N-methoxy-N-methylpropionamide (11)

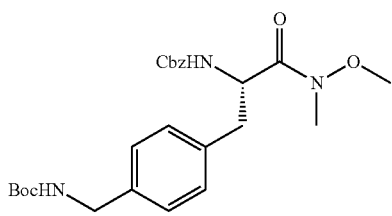 [SMILES: CON(C)C(=O)[C@H](Cc1ccc(CNC(=O)OC(C)(C)C)cc1)NC(=O)OCc1ccccc1]

Carboxylic acid 10 (4.45 g, 10.4 mmol) was dissolved in DCM (75 mL). To this were added NH(Me)OMe.HCl (1.5 eq., 15.6 mmol, 1.55 g), HCTU (1.5 eq., 15.6 mmol, 6.45 g) and DiPEA (4.5 eq., 46.7 mmol, 7.72 mL) and the mixture was stirred for 2 hours until TLC analysis indicated a completed reaction. The solvent was evaporated under reduced pressure and the residue was dissolved in EtOAc. This was extracted with 1 M aq. HCl (2×), saturated aq. Na$_2$CO$_3$ (2×) and brine, dried over MgSO$_4$ and concentrated under reduced pressure. The product was purified by column chromatography (10%→75% EtOAc/PE) and obtained as colourless oil (yield: 4.81 g, 10.2 mmol, 98%). $^1$H NMR (400 MHz, CDCl$_3$): δ=7.29-7.22 (m, 5H), 7.14 (d, J=8.12 Hz, 2H), 7.09 (d, J=8.17 Hz, 2H), 6.02 (d, J=8.49 Hz, 1H), 5.35 (s, 1H), 5.00 (dd, J=28.51, 12.34 Hz, 2H), 4.96-4.94 (m, 1H), 4.21 (d, J=5.20 Hz, 2H), 3.62 (s, 3H), 3.10 (s, 3H), 3.02 (dd, J=13.63, 5.63 Hz, 1H), 2.85 (dd, J=13.27, 7.70 Hz, 1H), 1.43 (s, 9H) ppm. $^{13}$C NMR (100 MHz, CDCl$_3$): δ=171.54, 155.50, 137.23, 136.02, 135.04, 129.04, 127.92, 127.48, 127.42, 126.98, 78.64, 66.11, 61.01, 51.78, 43.76, 37.46, 31.52, 27.96 ppm. $[\alpha]_d^{23}$=+10.1 (c=1, CHCl$_3$). HRMS: calcd. for C$_{25}$H$_{33}$N$_3$O$_6$ 472.24421 [M+H]$^+$. Found 472.24402.

(S)-Benzyl (1-(4-((tert-butyloxycarbonylamino)methyl)phenyl)-4-methyl-3-oxopent-4-en-2-yl)carbamate (12)

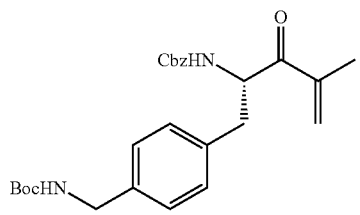 [SMILES: C=C(C)C(=O)[C@H](Cc1ccc(CNC(=O)OC(C)(C)C)cc1)NC(=O)OCc1ccccc1]

2-Bromopropene (3.5 eq., 14.0 mmol, 1.25 mL) was dissolved in THF (50 mL) and cooled to −78° C. tBuLi (6.5 eq., 26.0 mmol, 16.3 mL; 1.6 M in hexane) was added slowly and the mixture was stirred for 1 hour at −78° C. after which Weinreb amide 11 (1 eq., 4.0 mmol, 1.89 g) was added in THF (5 mL). The mixture was allowed to warm to −20° C. in 6 hours after which TLC analysis indicated complete consumption of the Weinreb amide. A saturated aqueous NH$_4$Cl solution and EtOAc were added and the layers were separated. The organic layer was extracted with brine, dried over MgSO$_4$ and concentrated under reduced pressure. The title compound was obtained after column chromatography (20%→50% EtOAc/PE) as a colourless oil (yield: 1.71 g, 3.77 mmol, 94%). $^1$H NMR (400 MHz, CDCl$_3$): δ=7.33-7.24 (m, 5H), 7.11 (d, J=7.87 Hz, 2H), 6.97 (d, J=8.00 Hz, 2H), 6.03 (s, 1H), 5.85 (s, 1H), 5.77 (d, J=8.18 Hz, 1H), 5.30 (dd, J=14.10, 6.11 Hz, 1H), 5.12-5.08 (m, 1H), 5.04 (dd, J=26.54, 12.35 Hz, 2H), 4.21 (d, J=5.41 Hz, 2H), 3.09 (dd, J=13.79, 5.88 Hz, 1H), 2.89 (dd, J=13.76, 5.97 Hz, 1H), 1.84 (s, 3H), 1.44 (s, 9H) ppm. $^{13}$C NMR (100 MHz, CDCl$_3$): δ=199.28, 155.66, 155.34, 141.99, 137.40, 136.13, 134.60, 129.27, 128.17, 127.80, 127.71, 126.50, 79.01, 66.45, 55.13, 43.96, 38.76, 28.14, 17.44 ppm. HRMS: calcd. for C$_{26}$H$_{32}$N$_2$O$_5$ 453.23840 [M+H]$^+$. Found 453.23818.

Benzyl((2S,3R)-1-(4-((tert-butyloxycarbonylamino)methyl)phenyl)-3-hydroxy-4-methylpent-4-en-2-yl)carbamate

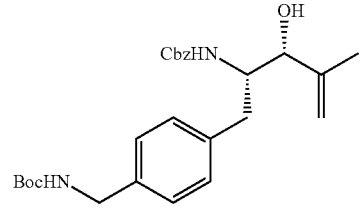 [SMILES: C=C(C)[C@@H](O)[C@H](Cc1ccc(CNC(=O)OC(C)(C)C)cc1)NC(=O)OCc1ccccc1]

Ketone 12 (2.81 g, 4.30 mmol) was dissolved in MeOH (25 mL) and cooled to 0° C. To this were added CeCl$_3$.7H$_2$O (1.5 eq., 6.45 mmol, 2.43 g) and NaBH$_4$ (1.4 eq., 6.0 mmol, 227 mg) portion-wise and the mixture was stirred for 5 minutes. after which TLC analysis indicated a complete conversion. Glacial acetic acid (10 mL) was added and the mixture was concentrated under reduced pressure. The resulting residue was dissolved in EtOAc and extracted with half saturated aq. NaHCO$_3$ (2×) and brine, dried over MgSO$_4$ and concentrated in vacuo. The title compound was obtained as a colourless oil (yield: 1.79 g, 3.94 mmol, 92%). $^1$H NMR (400 MHz, CDCl$_3$): δ=7.31-7.01 (m, 9H), 5.30 (d, J=9.18 Hz, 1H), 5.06 (s, 1H), 5.00 (d, J=5.19 Hz, 1H), 4.96-4.91 (m, 3H), 4.21 (d, J=4.41 Hz, 1H), 4.16-4.11 (m, 1H), 4.07-3.98 (m, 1H), 2.85 (d, J=12.55 Hz, 1H), 2.65 (dd, J=13.60, 10.41 Hz, 1H), 1.77 (s, 3H), 1.44 (s, 9H) ppm. $^{13}$C NMR (100 MHz, CDCl$_3$): δ=155.96, 155.85, 144.44, 137.34, 136.44, 129.34, 128.19, 127.77, 127.66, 127.25, 112.17, 79.25, 76.65, 66.27, 54.06, 44.15, 33.69, 28.22, 18.73 ppm. $[\alpha]_D^{23}=-18.7$ (c=1, CHCl$_3$). HRMS: calcd. for C$_{26}$H$_{34}$N$_2$O$_5$ 455.25405 [M+H]$^+$. Found 455.25392.

Benzyl((S)-3-(4-((tert-butyloxycarbonylamino) methyl) phenyl)-1-((R)-2-methyloxiran-2-yl)-1-oxopropan-2-yl) carbamate (14)

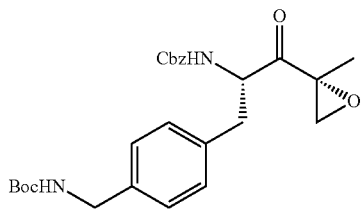

Allylic alcohol 13 (1.79 g, 3.94 mmol) was dissolved in DCM (25 mL) and cooled to 0° C. after which vanadyl acetylacetonate (0.1 eq., 0.4 mmol, 107 mg) and tBuOOH (3 eq., 12.0 mmol, 2.18 mL; 5.5 M in decane) were added and the mixture was stirred at 0° C. until TLC analysis indicated complete consumption of starting material after 2 hours. The mixture was concentrated under reduced pressure, redissolved in EtOAc and extracted with half sat. aq. NaHCO$_3$, H$_2$O and brine, dried over MgSO$_4$ and concentrated under reduced pressure. The resulting product was quickly purified by column chromatography (20%→60% EtOAc/PE) and immediately subjected to the next step because of the possible instability of the intermediate. The compound was dissolved in DCM (25 mL) and Dess-Martin periodinane (3 eq., 11.0 mmol, 4.50 g) was added. The mixture was stirred at room temperature for 12 hours after which TLC analysis indicated complete conversion. Next, a 1:4 (v/v) mixture (150 mL) of NaHCO$_3$ (sat. aq.)/Na$_2$S$_2$O$_3$ (1 M aq.) and the resulting emulsion was stirred vigorously for 30 minutes after which the layers were separated and the aqueous layer extracted with DCM. The combined organic layers were extracted with sat. aq. NaHCO$_D$ dried over MgSO$_4$ and concentrated under reduced pressure. The title compound was obtained after column chromatography (20%→30% EtOAc/PE) as a colourless oil (yield: 1.03 g, 2.20 mmol, 56%). $^1$H NMR (400 MHz, CDCl$_3$): δ=7.33-7.22 (m, 5H), 7.16 (d, J=7.94 Hz, 2H), 7.08 (d, J=7.95 Hz, 2H), 5.51 (d, J=8.19 Hz, 1H), 5.06-5.01 (m, 1H), 4.97 (d, J=4.39 Hz, 2H), 4.60 (dd, J=12.65, 7.86 Hz, 1H), 4.24 (d, J=4.36 Hz, 2H), 3.26 (d, J=4.62 Hz, 1H), 3.08 (dd, J=13.96, 4.48 Hz, 1H), 2.87 (d, J=4.53 Hz, 1H), 2.70 (dd, J=13.88, 8.12 Hz, 1H), 1.49 (s, 3H), 1.44 (s, 9H) ppm. $^{13}$C NMR (100 MHz, CDCl$_3$):δ=207.77, 155.74, 155.66, 137.61, 135.97, 134.62, 129.32, 128.26, 127.91, 127.76, 127.44, 79.15, 66.62, 58.99, 54.07, 52.12, 44.07, 36.61, 28.21, 16.34 ppm. $[\alpha]_D^{23}=+82.2$ (c=1, CHCl$_3$).

tert-Butyl 4-((S)-2-amino-3-((R)-2-methyloxiran-2-yl)-3-oxopropyl)benzylcarbamate TFA salt (15)

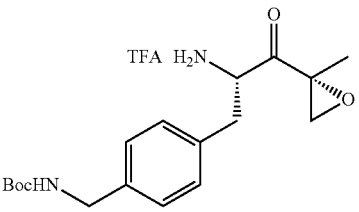 [SMILES: CC(C)(C)OC(=O)NCc1ccc(C[C@H](N)C(=O)[C@@]2(C)CO2)cc1]

Cbz-protected amine 14 (107 mg, 0.23 mmol) was dissolved in MeOH (5 mL) and to this was added TFA (1.2 eq., 0.27 mmol, 21 µL). Argon was bubbled through the solution for 15 minutes, after which Pd black (10 mg) was added and the flask was charged with hydrogen gas. After 10 minutes, TLC analysis indicated complete conversion of starting material and all solids were removed by filtration over CELITE. Toluene (10 mL) was added and the mixture was concentrated under reduced pressure followed by coevaporation with toluene (2×) in order to remove excess TFA. The purity of the deprotected amine (as TFA salt) was confirmed by LC-MS analysis and the compound was subjected to the next step without further purification.

(S)-tert-butyl 4-(3-(methoxy(methyl)amino)-3-oxo-2-(tritylamino)propyl)benzylcarbamate (16)

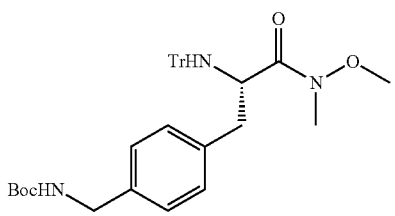

Compound 11 (1.43 g, 3.04 mmol) was dissolved in a 50:1 mixture EtOH/AcOH (25 mL) and argon was bubbled through this solution for 15 minutes. Next, Pd/C (10% w/w, 0.1 g) was added and hydrogen was bubbled through the mixture until TLC indicated complete consumption of starting material after 4 hours. Argon was bubbled through for another 15 minutes after which the mixture was filtered over CELITE and the filtrate concentrated under reduced pressure. The deprotected amine (as AcOH salt) was obtained in a crude yield of 1.21 g (max. 3.04 mmol) and was subsequently dissolved in DCM (20 mL). To this were added Et$_3$N (2 eq., 6.08 mmol, 0.85 mL), DMAP (0.1 g) and tritylchloride (1.5 eq., 4.56 mmol, 1.30 g). The mixture was stirred for 6 hours after which it was concentrated under reduced pressure, redissolved in EtOAc and extracted with 10 mM aq. HCl and brine, dried over MgSO$_4$ and concentrated under reduced pressure. The resulting mixture was purified by column chromatography (10%→50% EtOAc/PE) and the title compound was obtained as colourless foam (yield: 0.68 g, 1.17 mmol, 38%). $^1$H NMR (400 MHz, CDCl$_3$): δ=7.47 (s, 1H), 7.34 (d, J=7.33 Hz, 6H), 7.26-7.20 (m, 4H), 7.18-7.05 (m, 9H), 5.10 (s, 1H), 4.28 (s, 2H), 4.00 (t, J=5.60, 5.60 Hz, 1H), 3.18 (s, 3H), 2.92 (dd, J=13.24, 5.63 Hz, 1H), 2.77 (dd, J=12.93, 7.51 Hz, 1H), 2.63 (s, 3H), 1.44 (s, 9H) ppm. $^{13}$C NMR (100 MHz, CDCl$_3$): δ=174.80, 155.74, 145.92, 137.18, 137.13, 130.25, 128.70, 127.33, 127.15, 125.86, 79.07, 70.59, 60.00, 54.09, 44.19, 41.86, 31.96, 28.20 ppm. [α]$_D^{23}$=+58.6 (c=1, CHCl$_3$).

(S,E)-tert-butyl 4-(4-(methylsulfonyl)-2-(tritylamino)but-3-en-1-yl)benzylcarbamate (17)

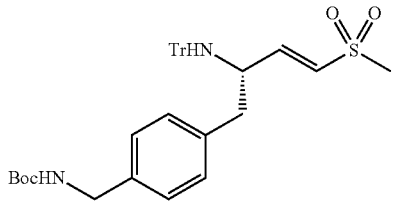

Weinreb amide 16 (0.65 g, 1.12 mmol) was dissolved in Et$_2$O (15 mL), put under an argon atmosphere and cooled to 0° C. LiAlH$_4$ (2 eq., 2.25 mmol, 0.56 mL of a 4 M solution in Et$_2$O) was added slowly and the mixture was stirred at 0° C. for 1 hour after which TLC analysis indicated complete conversion of the starting compound. 0.1 M aq. HCl (15 mL) was slowly added and the layers were separated. The organic layer was extracted with 0.1 M aq. HCl and brine, dried over MgSO$_4$ and concentrated under reduced pressure. Diethyl ((methylsulfonyl)methyl)phosphonate (1.5 eq., 1.68 mmol, 0.39 g) was dissolved in THF (20 mL) and cooled to 0° C. under an argon atmosphere. NaH (1.5 eq., 1.68 mmol, 67.2 mg, 60% w/w in mineral oil) was slowly added and the mixture was stirred at 0° C. for 30 minutes. Next, the freshly obtained aldehyde (in THF (2 mL)) was slowly added and the mixture was stirred for 2 hours while slowly warming it to room temperature. After this time TLC analysis indicated complete conversion of the aldehyde. EtOAc (20 mL) was added and the mixture was extracted with mM aq. HCl (2×) and brine, dried over MgSO$_4$ and concentrated under reduced pressure. The title compound was obtained after column chromatography (20%→50% EtOAc/PE) as a colourless foam (yield: 0.57 g, 0.95 mmol, 85%). $^1$H NMR (400 MHz, CDCl$_3$): δ=7.46 (d, J=7.6 Hz, 6H), 7.28 (t, J=7.20, 6.80 Hz, 6H), 7.20 (t, J=7.20, 7.20 Hz, 3H), 7.13 (d, J=7.60 Hz, 2H), 6.87 (d, J=8.00 Hz, 2H), 6.57 (dd, J=14.80, 7.00 Hz, 1H), 5.96 (d, J=14.80 Hz, 1H), 4.80 (s, 1H), 4.24 (d, J=5.60 Hz, 2H), 3.49 (q, J=6.00 Hz, 1H), 2.61 (s, 3H), 2.54 (dd, J=13.20, 5.20 Hz, 1H), 2.33 (dd, J=13.20, 8.20 Hz, 1H), 1.44 (s, 9H) ppm. $^{13}$C NMR (100 MHz, CDCl$_3$): δ=155.59, 150.21, 145.74, 137.42, 135.28, 129.53, 128.35, 128.02, 127.70, 127.14, 126.44, 78.91, 71.05, 55.33, 43.79, 42.43, 41.86, 28.09 ppm. [α]D=−21.3 (c=1, CHCl$_3$). HRMS: calcd. for C$_{36}$H$_{40}$N$_2$O$_4$S 619.26010 [M+Na]$^+$. Found 619.26001.

(S,E)-tert-butyl 4-(4-(methylsulfonyl)-2-aminobut-3-en-1-yl)benzylcarbamate (18)

Trityl protected amine 17 (0.54 g, 0.90 mmol) was treated with 1% v/v TFA/DCM (15 mL) at room temperature. To this yellow solution was added H$_2$O (1 mL) which resulted in a colourless suspension. After stirring the mixture for 30 minutes, 10 mM aq. HCl (20 mL) was added and DCM was removed under reduced pressure. The aqueous layer was extracted with Et$_2$O (3×) and basified with NaHCO$_3$ until pH 9, after which it was extracted with DCM (3×). The latter combined organic layers were dried over MgSO$_4$ and concentrated under reduced pressure. The resulting deprotected amine proved to be pure on LC-MS analysis and was subjected to the next step without further purification.

N$_3$Phe-Leu-Leu-Phe (4-CH$_2$NH$_2$) VS (SEQ ID NO:4) TFA salt (4a)

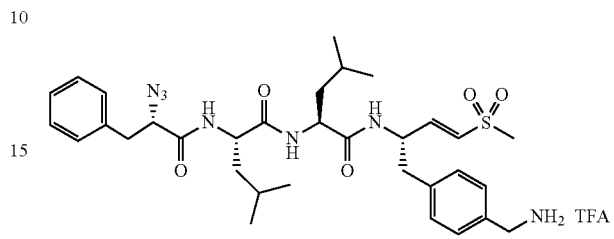

This compound was synthesized according to General procedure I on a 100 µmol scale by addition of amine 18. The title compound was obtained after RP-HPLC purification (gradient: 20%→60% MeOH/0.1% aq. TFA) as a colourless solid (yield: 15.4 mg, 20.1 µmol, 20%). $^1$H NMR (400 MHz, CD$_3$OD): δ=7.39-7.21 (m, 9H), 6.78 (dd, J=15.20, 5.34 Hz, 1H), 6.55 (dd, J=15.21, 1.52 Hz, 1H), 4.82-4.77 (m, 1H), 4.36-4.27 (m, 2H), 4.17 (dd, J=8.61, 4.80 Hz, 1H), 4.07 (s, 2H), 3.19 (dd, J=14.05, 4.75 Hz, 1H), 3.02-2.95 (m, 3H), 2.92 (s, 3H), 1.63-1.43 (m, 6H), 0.93 (t, J=5.65, 5.65 Hz, 6H), 0.88 (d, J=6.24 Hz, 6H) ppm. $^{13}$C NMR (100 MHz, CD$_3$OD): δ=174.45, 174.27, 171.95, 146.65, 139.63, 137.85, 133.01, 131.90, 131.30, 130.47, 130.26, 129.67, 128.13, 65.56, 53.74, 53.49, 52.46, 44.11, 42.83, 41.80, 41.61, 40.29, 38.71, 25.95, 25.86, 23.47, 23.46, 21.96, 21.94 ppm. LC-MS: R$_t$ (min): 6.99 (ESI-MS (m/z): 654.20 (M+H$^+$)). HRMS: calcd. for C$_{33}$H$_{47}$N$_7$O$_5$S 654.34321 [M+H]$^+$. Found 654.34322.

N$_3$Phe-Leu-Leu-Phe(4-CH$_2$NH$_2$)EK (SEQ ID NO:5) TFA salt (4b)

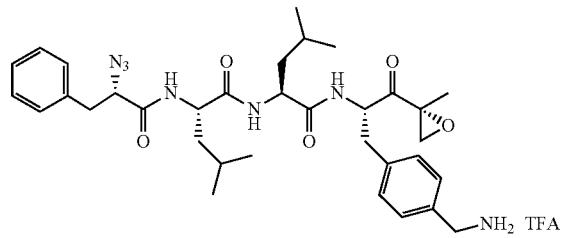 [SMILES: CC(C)C[C@H](NC(=O)[C@H](Cc1ccccc1)N=[N+]=[N-])C(=O)N[C@@H](CC(C)C)C(=O)N[C@@H](Cc1ccc(CN)cc1)C(=O)[C@@]1(C)CO1]

This compound was synthesized according to General procedure I on a 100 µmol scale by addition of amine 15. The title compound was obtained after RP-HPLC purification (gradient: 20% 60% MeOH/0.1% aq. TFA) as a colourless solid (yield: 17.6 mg, 23.5 µmol, 24%). $^1$H NMR (400 MHz, CD$_3$OD): δ=7.36-7.20 (m, 9H), 4.68 (dd, J=9.34, 4.20 Hz, 1H), 4.38-4.28 (m, 2H), 4.12 (dd, J=8.58, 4.79 Hz, 1H), 4.05 (s, 2H), 3.21 (d, J=4.97 Hz, 1H), 3.15 (dd, J=14.18, 4.69 Hz, 1H), 3.08 (dd, J=13.84, 4.06 Hz, 1H), 2.95-2.87 (m, 2H), 2.72 (dd, J=13.90, 9.34 Hz, 1H), 1.52-1.43 (m, 6H), 1.41 (s, 3H), 0.94-0.83 (m, 12H) ppm. $^{13}$C NMR (100 MHz, CD$_3$OD): δ=208.54, 174.48, 174.13, 171.69, 139.71, 137.87, 132.95, 131.15, 130.47, 130.14, 129.65, 128.10, 65.59, 60.25, 54.51, 53.40, 53.15, 52.79, 44.14, 42.13, 41.79, 38.73, 37.11, 25.83, 23.49, 22.03, 21.94, 16.81 ppm. LC-MS: $R_t$ (min): 7.36 (ESI-MS (m/z): 634.20 (M+H$^+$)). HRMS: calcd. for $C_{34}H_{47}N_7O_5$ 634.37114 [M+H]$^+$. Found 634.37090.

Bodipy-triazole-Phe-Leu-Leu-Phe (4-CH$_2$NH$_2$) VS (SEQ ID NO:7) TFA salt (39)

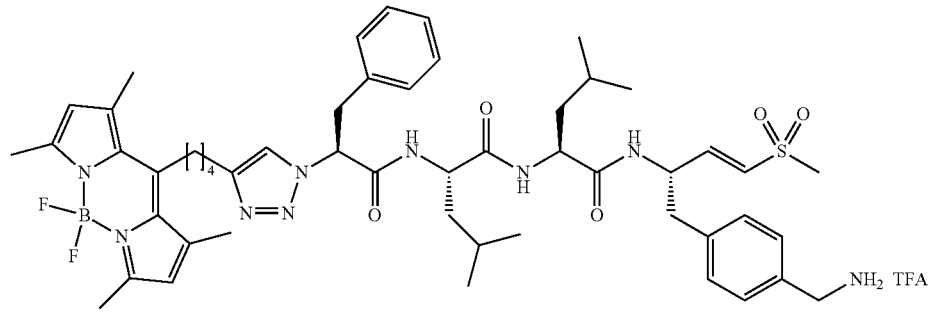

Compound 4a (5.68 mg, 8.69 μmol) and Bodipy-alkyne (1.5 eq., 13.0 μmol, 4.28 mg) were dissolved in a 1:1:1 mixture of H$_2$O/tBuOH/Tol (1.5 mL) and to this were added CuSO$_4$ (0.1 eq., 0.87 μmol, 0.87 μL of a 1M solution in H$_2$O) and sodium ascorbate (0.15 eq., 1.3 μmol, 1.3 μL of a 1M solution in H$_2$O) and the reaction was stirred at 80° C. for 4 hours. LC-MS analysis revealed complete consumption of the azide and formation of a single product ($R_t$ (min.): 10.41 (ESI-MS (m/z): 981.20 (M+H$^+$))), which was assigned to be the corresponding benzaldehyde. The mixture was concentrated under reduced pressure and dissolved in MeOH (1.5 mL). To this were added NH$_4$OAc (10 eq., 70 μmol, 5.4 mg) and NaCNBH$_4$ (2 eq., 15 μmol, 1.0 mg) and the reaction was stirred for 15 hours, after which LC-MS analysis indicated a complete disappearance of the aldehyde peak. The reaction was quenched by addition of aqueous HCl (100 μL, 1M) and the mixture was concentrated under reduced pressure. The title compound was obtained after RP-HPLC purification (gradient: 30%→70% ACN/0.1% aq. TFA) as a red/brown solid (yield: 2.1 mg, 2.14 μmol, 29%). $^1$H NMR (400 MHz, CD$_3$OD): δ=7.77 (s, 1H), 7.31 (d, J=7.91 Hz, 2H), 7.25 (d, J=8.08 Hz, 2H), 7.03-6.97 (m, 5H), 6.75 (dd, J=15.17, 5.40 Hz, 1H), 6.50 (dd, J=15.26, 1.28 Hz, 1H), 6.08 (s, 2H), 5.52 (dd, J=10.52, 5.15 Hz, 1H), 4.85-4.81 (m, 1H), 4.29-4.22 (m, 2H), 3.95 (s, 2H), 3.37-3.34 (m, 2H), 2.97-2.91 (m, 4H), 2.87 (s, 3H), 2.72-2.67 (m, 2H), 2.40 (s, 6H), 2.33 (s, 6H), 1.88-1.79 (m, 2H), 1.64-1.41 (m, 8H), 0.93-0.75 (m, 12H) ppm. LC-MS: $R_t$ (min): 8.42 (ESI-MS (m/z): 982.40 (M+H$^f$)). HRMS: calcd. for $C_{52}H_{70}BF_2N_9O_5S$ [M+H]$^+$ 982.53545. Found 982.53653.

(Val-Ser-Phe (4-CH$_2$NH$_2$)-methyl vinyl sulfone)-3-hydroxy-2-methylbenzamide (40)

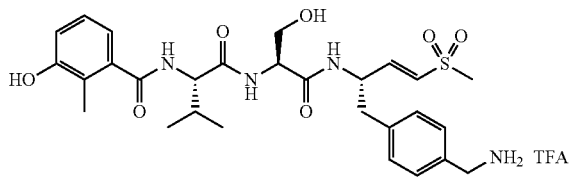 [SMILES: Cc1c(O)cccc1C(=O)N[C@H](C(=O)N[C@@H](CO)C(=O)N[C@H](/C=C/S(C)(=O)=O)Cc1ccc(CN)cc1)C(C)C]

This compound was synthesized according to General procedure I on a 245 μmol scale by addition of amine 18. The title compound was obtained after RP-HPLC purification (gradient: 10%→25% ACN/0.1% aq. TFA) as a colourless solid (yield: 57.3 mg, 83.2 μmol, 34%). $^1$H NMR (400 MHz, CD$_3$OD):δ=7.22 (d, J=8.48 Hz, 2H), 7.19 (d, J=8.45 Hz, 2H), 6.95 (t, J=7.80 Hz, 1H), 6.77-6.69 (m, 3H), 6.65 (dd, J=15.17, 1.46 Hz, 1H), 4.81-4.76 (m, 1H), 4.29 (t, J=5.53 Hz, 1H), 4.17 (d, J=7.16 Hz, 1H), 3.90 (d, J=5.45 Hz, 2H), 3.69 (dd, J=10.78, 5.01 Hz, 1H), 3.60 (dd, J=10.76, 6.19 Hz, 1H), 2.92 (dd, J=13.83, 6.47 Hz, 1H), 2.84-2.80 (m, 1H), 2.82 (s, 3H), 2.10-2.01 (m, 1H), 2.06 (s, 3H), 0.89 (dd, J=6.67, 4.95 Hz, 6H) ppm. $^{13}$C NMR (100 MHz, CD$_3$OD): δ=174.00, 173.61, 171.83, 157.08, 146.95, 139.62, 139.11, 132.93, 131.78, 131.18, 130.18, 127.60, 123.26, 119.16, 117.19, 62.90, 61.62, 56.49, 52.60, 44.04, 42.84, 40.16, 31.40, 19.89, 19.06, 13.06 ppm. LC-MS: $R_t$ (min): 4.19 (ESI-MS (m/z): 575.20 (M+H$^+$)). HRMS: calcd. for $C_{28}H_{38}N_4O_7S$ [M+H]$^+$ 575.25340. Found 575.25336.

Biological Evaluation: Competition Assays in Cell Lysate.

Whole cell lysates of HEK-293T or EL-4 cells were made by sonication in 3 volumes of lysis buffer containing 50 mM Tris pH 7.5, 1 mM DTT, 5 mM MgCl$_2$, 250 mM sucrose, 2 mM ATP, 0.025% digitonin. Protein concentration was determined by the Bradford assay. Cell lysates (13.5 μg total protein for HEK lysates and 9 μg total protein for EL-4 lysates) were exposed to the inhibitors for 1 hour at 37° C. prior to incubation with MV151 (0.5 μM) for 1 hour at 37° C. Reaction mixtures were boiled with Laemmli's buffer containing β-mercaptoethanol for 5 minutes before being resolved by 12.5% SDS-PAGE. In-gel detection of residual proteasome activity was performed in the wet gel slabs directly on the TYPHOON Variable Mode Imager (Amersham Biosciences) using the Cy3/Tamra settings ($\lambda_{ex}$ 532 nm, $\lambda_{em}$ 560 nm) to detect MV151 and Cy2/Fam settings ($\lambda_{ex}$ 488 nm, $\lambda_{em}$ 520 nm) to detect compound 39.

Biological Evaluation: Competition Assays in Living Cells.

Human embryonic kidney cells (some 1×10$^6$) were cultured in 6-well plates in DMEM containing 10% fetal calf serum, 10 units/mL penicillin and 10 μg/mL streptomycin in a 7% CO$_2$ humidified incubator at 37° C. overnight. Part of the medium was taken and to this was added the appropriate inhibitor in DMSO (1 μL of a 1,000× stock solution), after which the medium was added to the cells. The cells were incubated with the inhibitors for 4 hours at 37° C. and this was followed by addition of MV151 (1 μL of a 5 mM stock solution in DMSO) and incubation for 2 hours at 37° C. Next, the medium was removed and the cells were washed with PBS and harvested. After flash freezing in liquid N$_2$, the cells were resuspended in 4 volumes of homogenation buffer (50 mM Tris pH 7.5, 250 mM sucrose, 5 mM $MgCl_2$, 1 mM DTT, 2 mM ATP, 0.025% digitonin) containing 10 μM AdaKBio, sonicated (12 W, 1 minute) and centrifuged at 16,000 rcf at 0° C. for 20 minutes. The supernatant was collected and the protein concentration was determined by the Bradford assay. All samples were normalized to the same protein concentration with lysis buffer. After boiling the samples with Laemmli's buffer containing β-mercaptoethanol for 5 minutes and resolving by 12.5% SDS-PAGE the residual proteasome activity was detected as described above.

Example 10

Evaluation of Epoxyketones and Vinyl Sulfones with 4-Aminomethylene-L-Phenylalanine in the P1 Position Retro-synthetically, the modified oligopeptides can be prepared from tripeptide hydrazide $N_3$Phe-Leu-Leu-$NHNH_2$ and the properly protected warhead amines in an (epimerization free) azide coupling. The synthesis of P1-benzyl amine containing vinyl sulfone and epoxyketone warheads leading to inhibitors 4a and 4b is shown in Scheme 3. The synthetic scheme commenced with the introduction of the aminomethylene substituent on L-phenylalanine 8, by performing an electrophilic aromatic substitution with N-(hydroxymethyl) trichloroacetamide under acidic conditions. In this reaction both the ortho and the para substituted isomers were formed, which could be separated by column chromatography. The desired para substituted isomer was obtained in 35% yield. After Cbz-protection of the α-amine, compound 9 was obtained. Basic removal of the trichloroacetamide group followed by Boc protection of the formed amine gave 10, which was coupled to N,O-dimethylhydroxylamine to give Weinreb-amide 11. Upon a reaction with 2-lithiumpropene the α',β'-unsaturated ketone 12 was obtained. Stereoselective reduction to the allylic alcohol 13 and subsequent asymmetric epoxidation and Dess-Martin oxidation resulted in epoxyketone 14. This compound was α-amine deprotected by hydrogenation, which finalized the synthesis of compound 15. The vinylsulfone analogue was created by α-amine deprotection of compound II, followed by tritylation (16). Reduction of the Weinreb-amide, followed by a Horner-Wadworth-Emmons reaction and de-tritylation finally resulted in compound 18.

SCHEME 3

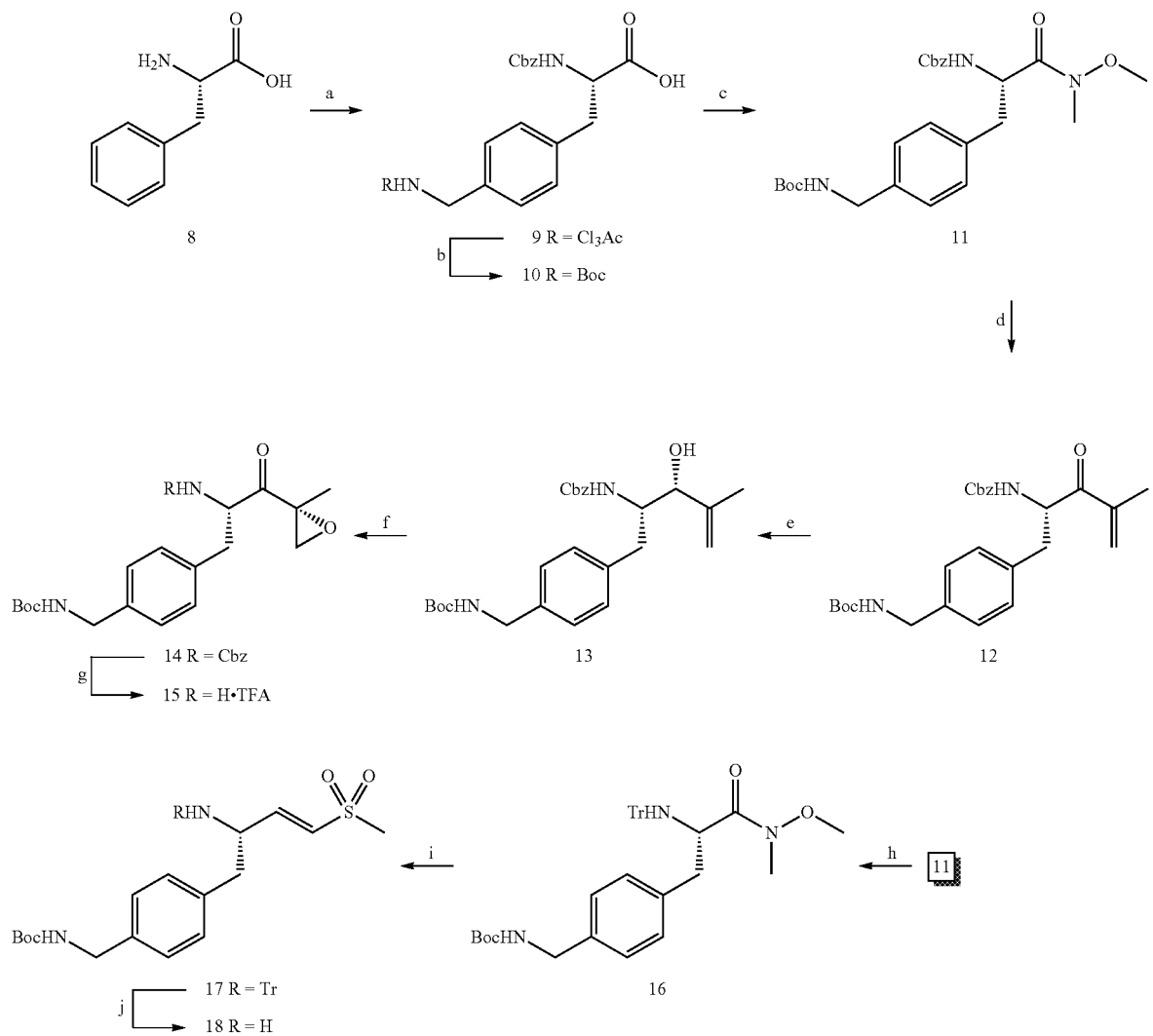

Reagents and conditions in Scheme 3 are as follows: (a) i) N-(hydroxymethyl)trichloroacetamide, $H_2SO_4$, $H_2O$; ii) benzyl chloroformate, $Na_2CO_3$, $H_2O$, 1,4-dioxane, 35%; (b) i) 20% NaOH, EtOH/$H_2O$ 1:1; ii) $Boc_2O$, $Na_2CO_3$, THF, $H_2O$, 75%; (c) NH(Me)OMe.HCl, HCTU, DiPEA, DCM, 98%; (d) 2-bromopropene, tBuLi, THF, −78° C., 94%; (e) $NaBH_4$, $CeCl_3$.$7H_2O$, MeOH, 0° C., 92%; (f) i) tBuOOH, VO($Acac$)$_2$, DCM, 0° C.; ii) Dess-Martin periodinane, DCM, 56%; (g) $H_2$, Pd black, TFA, MeOH; (h) i) $H_2$, Pd/C, AcOH, EtOH; ii) TrCl, $Et_3N$, DMAP, DCM, 38%; (i) i) $LiAlH_4$, $Et_2O$, 0° C.; ii) diethyl ((methylsulfonyl)methyl)phosphonate, NaH, THF, 0° C., 85%; (j) 1% TFA/DCM.

Scheme 4 shows the azide coupling of amine warheads 18 and 24 with tripeptide hydrazide 38, giving, after TFA-mediated deprotection and RP-HPLC purification, inhibitor 4a. The other inhibitors were made in a similar reaction from the appropriate amines in varying yields of 7-48% after RP-HPLC. LC-MS and NMR analysis showed for neither compound any sign of epimerization of the final products.

The inhibition potential of the inhibitors for each of the catalytically active subunits was assessed in competition assays employing extracts of human embryonic kidney cells (HEK-293T) and mouse lymphoma cells (EL-4) in combination with the fluorescent broad spectrum proteasome probe MV151 (Verdoes, et al. (2006) Chem. Biol. 13:1217-1226). Competitive inhibition of a proteasome active site is reflected by the disappearance of the corresponding band on a gel.

SCHEME 4

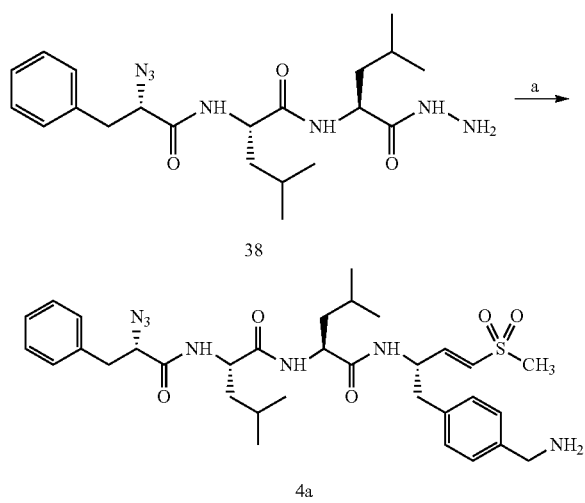

Reagents and conditions in Scheme 4 are as follows: (a) i) tBuONO, HCl, DMF, DCM, −30° C.; ii) compound 18 or 24, DiPEA; iii) TFA, DCM, then RP-HPLC, yields: 7-48%.

Compound 4a was tested for their capability to cross the cell membrane. Living HEK-293T cells were incubated with each of the three inhibitors at 0.5, 5 and 50 µM final concentrations for 4 hours, after which all residual proteasome activity was labelled with cell permeable probe MV151. The cells were lysed, all proteins denatured and resolved by SDS-PAGE. As a control the broad-spectrum proteasome inhibitor AdaAhx$_3$L$_3$VS (Kessler, et al. (2001) Chem. Biol. 8:913-929b), which is known to be able to cross the cell membrane, was used. The results indicated that the primary amine in compound 4a does not result in inpermeability toward the cell membrane and is still able of inhibiting (almost) all β2 activity at 5 µM.

For direct labelling of β2 a new fluorescent probe was made by reacting compound 4a with a green fluorescent Bodipy-alkyne (Verdoes, et al. (2007) Bioorg. Med. Chem. Lett. 17:6169-6171) in a 'click' reaction. This reaction however was not as straightforward as could be expected from earlier results. Upon reaction of both compounds with $CuSO_4$ and sodium ascorbate in an aqueous medium compound 4a was completely consumed, however the formed product had a mass of one Dalton less compared to the expected product mass and it was dramatically more hydrophobic compared to the starting material, as evidenced from LC-MS measurements. It was reasoned that the free benzylic amine was oxidized and hydrolyzed into its corresponding benzaldehyde. This reaction has been previously observed (Srogl & Voltrova (2009) Org. Lett. 11:843-845), wherein a copper/ascorbic acid dyad catalytic system for the selective aerobic oxidation of amines (both benzylic and aliphatic). Indeed, upon addition of ammonium acetate and $NaCNBH_3$ a reductive amination took place, resulting in the desired product 39.

The ability of compound 39 to label proteasome actives both in HEK-293T cell lysate and living cells was assessed in a competition assay as described herein. A dual-wavelength fluorescence read-out was performed allowing visualisation of one of the two fluorescent dyes at a time. From this analysis it becomes clear that the introduction of the bulky, hydrophobic BODIPY moiety results in the loss of the inhibitor's selectivity for β2 over β5. Both subunits are inhibited equally well, leaving only β1 untouched. Probably the large hydrophobic moiety is too close to the active site and introduction of a spacer between tag and warhead may reinstall β2 selectivity. Interestingly, introduction of the BODIPY has had a detrimental effect on cell permeability. At a concentration of 5 µM both subunits (β2 and β5) seem not to be competed away at all, although a faint band for each subunit is visible in the lower gel. Even at a concentration of 50 µM not all proteasome activity is silenced. This observation must come from the cell penetrating properties of the probe, since all β2 and β5 proteasomal activity is inhibited at a 5 µM concentration in cell lysate.

As discussed, vinyl ethyl ester tripeptide HMB-VSL-VE 2 has been identified as a potent, cell permeable β2 selective inhibitor (Marastoni, et al. (2005) J. Med. Chem. 48:5038-5042; Baldisserotto, et al. (2007) Eur. J. Med. Chem. 42:586-592). Other inhibitors containing the vinyl ethyl ester warhead have been made, which are known to target other subunits as well (Baldisserotto, et al. (2009) Bioorg. Med. Chem. 17:5535-5540). It is therefore likely that the majority of the β2 selectivity comes from the unique HMB-Val-Ser peptide sequence. For this reason, a combination of the HMB-Val-Ser peptide sequence and the P1-functionalized warheads discussed so far may result in inhibitors with an even enhanced preference for the β2(i) subunit. To this end compounds 40 and 41 were synthesized via the method outlined above from HMB-Val-Ser(tBu)—$NHNH_2$. First, both compounds were tested for their inhibitory activity in HEK-293T cell lysate in a competition assay as discussed earlier. When comparing compound 40 and 4a, it becomes clear that substitution of the $N_3$PheLeu$_2$ for the HMB-Val-Ser motif decreased the general potency by a factor two. In addition, the selectivity for β2 over β5 is substantially increased. Only a part of the β5 activity is inhibited at 50 µM by 40, whereas compounds 4a completely blocks β5 at this concentration. This difference is even more pronounced for the inhibition in living cells by 40. The β2 band has almost disappeared at a concentration of 5 µM and β5 is not affected at all at concentrations up to 50 µM. The most striking result from this assay is the apparent selectivity of compound 40 for β2 over β2i in EL-4 lysate. At a concentration of 0.5 μM β2 is almost completely blocked, whereas the compound starts to inhibit β2i only at 5 μM. The characteristics in terms of selectivity remain unchanged (it still targets both β2 and β5). These observations invite the conclusion that the HMB-Val-Ser sequence on its own is not enough to active β2 selectivity, but that by selection of a suitable P1 substituent this objective might be reached after all.

Example 11

PR-671A Overcomes Bortezomib Resistance

The activity of compound 4a (PR671A) was further tested in combination with β5 selective proteasome inhibitors, bortezomib or PR523 (i.e., LU-005). Using myeloma cells, U266 and AMO-1, it was found that the combination of PR671A and either bortezomib or PR523 results in synergistic cytotoxicity against the myeloma cells (FIG. 1A-1D).

Figure 2A:
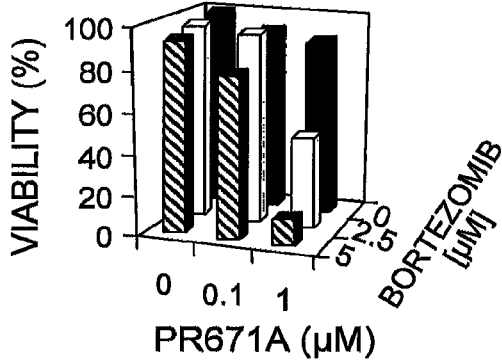
FIG. 2 shows that compound 4a (PR671A) in combination with β5-selective proteasome inhibitors, bortezomib (FIGS. 2A and 2C) or PR523 (i.e., LU-005.
FIGS. 2B and 2D) overcomes bortezomib resistance in bortezomib-adapted myeloma cell lines, AMO-1a (FIGS. 2A and 2B) and HL-60a (FIGS. 2C and 2D), and bortezomib-refractory primary myeloma cells from three different patients (FIGS. 2E-2G).
Figure 2C:
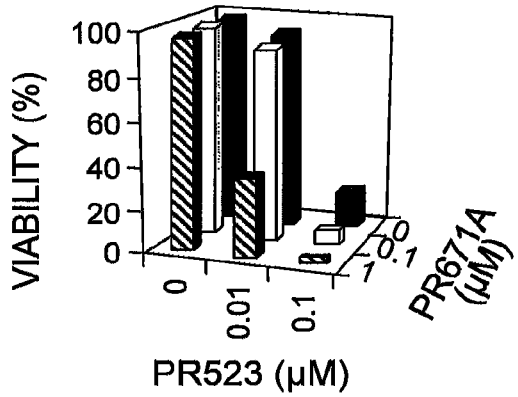
Figure 2B:
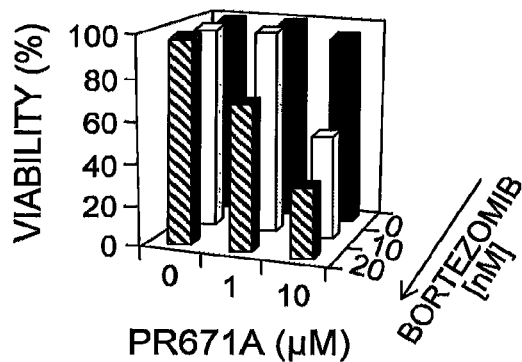
Figure 2D:
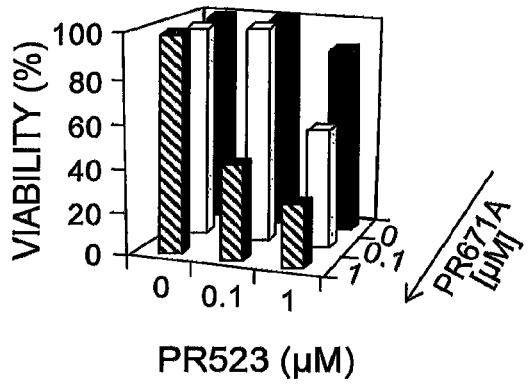
Figure 2E:
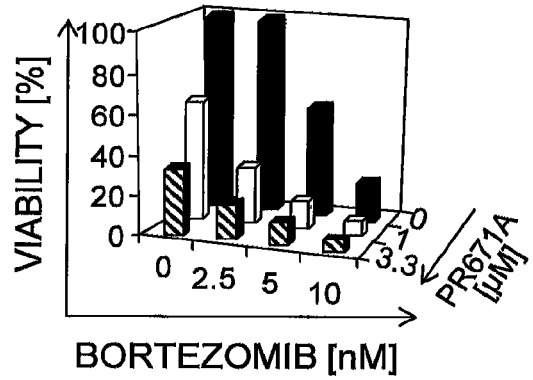
Figure 2F:
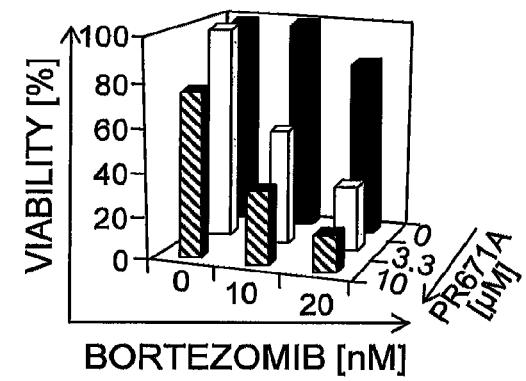
Figure 2G:
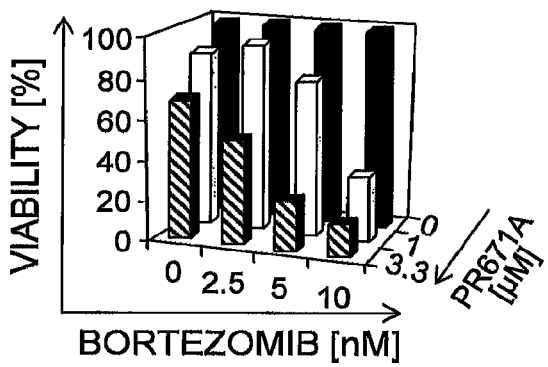

Furthermore, compound 4a (PR671A) in combination with β5-selective proteasome inhibitors, bortezomib (FIGS. 2A and 2C) or PR523 (i.e., LU-005; FIGS. 2B and 2D) was shown to overcomes bortezomib resistance in bortezomib-adapted myeloma cell lines, AMO-1a (FIGS. 2A and 2B) and HL-60a (FIGS. 2C and 2D), and bortezomib-refractory primary myeloma cells from three different myeloma patients exhibiting resistance to bortezomib (FIGS. 2E-2G).

What is claimed is:

1. A peptide-based inhibitor of the proteasome β2/β2i site comprising the structure:

(Y)-(X4)-X3-X2-X1        (SEQ ID NO:2), wherein X1 is an arginine residue with an epoxyketone or vinyl sulfone warhead or X1 is a 4-aminomethylene-L-phenylalanine residue with an epoxyketone or vinyl sulfone warhead; X2 is Leu or Ser, X3 is Leu, Val, Arg, or 4-aminomethylene-L-Phe, wherein X4 is present or absent and when present is Phe; and Y is present or absent and when present is a capping group.

2. The peptide-based inhibitor of claim 1, wherein the capping group is a label.

3. A pharmaceutical composition comprising the peptide-based inhibitor of claim 1 and a pharmaceutically acceptable carrier.

4. The pharmaceutical composition of claim 3, further comprising an inhibitor of the proteasome β5/β5i site.

5. A method for inhibiting the activity of the β2/β2i site of a proteasome comprising contacting a proteasome with a peptide-based inhibitor of claim 1 so that activity of the proteasome β2/β2i site is inhibited.

6. A method for treating cancer, organ graft rejection, an auto-immune disease, parasitic disease or inflammatory condition comprising administering to a subject in need of treatment an effective amount of the pharmaceutical composition of claim 3 thereby treating the subject's cancer, organ graft rejection, an auto-immune disease, parasitic disease or inflammatory condition.

7. The method of claim 6, further comprising administering an inhibitor of the proteasome β5/β5i site.

8. A method for producing the peptide based inhibitor of claim 1, comprising
   (a) protecting amine groups of arginine or a 4-aminomethylene-L-phenylalanine residue,
   (b) introducing an epoxyketone or vinyl sulfone warhead onto the arginine or 4-aminomethylene-L-phenylalanine residue, and
   (c) attaching a proteasomal β2/β2i site-selective oligopeptide to the alpha amino-group of the arginine or 4-aminomethylene-L-phenylalanine so that a peptide-based inhibitor is produced.

* * * * *

UNITED STATES PATENT AND TRADEMARK OFFICE
CERTIFICATE OF CORRECTION

PATENT NO.         : 8,455,431 B2
APPLICATION NO.    : 13/399189
DATED              : June 4, 2013
INVENTOR(S)        : Alexei Kisselev et al.

Page 1 of 1

It is certified that error appears in the above-identified patent and that said Letters Patent is hereby corrected as shown below:

On the Title page, at item (73), please delete "Dartmout"

On the Title page, at item (73), please add --Dartmouth--

On the Title page, at item (74), please delete "Tyrell"

On the Title page, at item (74), please add --Tyrrell--

Signed and Sealed this
Sixth Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,455,431 B2
APPLICATION NO. : 13/399189
DATED : June 4, 2013
INVENTOR(S) : Kisselev et al.

Page 1 of 1

It is certified that error appears in the above-identified patent and that said Letters Patent is hereby corrected as shown below:

In the Specification

Column 1, please delete Lines 9-12 and insert in its place the following:
--This invention was made with government support under grant number R01 CA124634 awarded by the National Institutes of Health. The government has certain rights in the invention.--

Signed and Sealed this
Twenty-eighth Day of April, 2020

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Modified with vinyl sulfone warhead.

<400> SEQUENCE: 1

Tyr Arg Leu Asn
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Arg or 4-aminomethylene-L-Phe. Xaa is
      modified with a epoxyketone or vinyl sulfone warhead.
<220> FEATURE:
<221> NAME/KEY: MISC_FEATURE
<222> LOCATION: (2)..(2)
<223> OTHER INFORMATION: Xaa is Leu or Ser.
<220> FEATURE:
<221> NAME/KEY: MISC_FEATURE
<222> LOCATION: (3)..(3)
<223> OTHER INFORMATION: Xaa is Leu, Val, Arg, or
      4-aminomethylene-L-Phe.
<220> FEATURE:
<221> NAME/KEY: MISC_FEATURE
<222> LOCATION: (4)..(4)
<223> OTHER INFORMATION: Xaa is present or absent and when present is
      Pro, Tyr or Phe. Xaa can further include a capping group

<400> SEQUENCE: 2

Xaa Xaa Xaa Xaa
1

<210> SEQ ID NO 3
<211> LENGTH: 4
<212> TYPE: PRT
```

-continued

```
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aza-Glycine
<220> FEATURE:
<221> NAME/KEY: MOD_RES
<222> LOCATION: (4)..(4)
<223> OTHER INFORMATION: Modified with epoxyketone warhead.

<400> SEQUENCE: 3

Gly Leu Leu Arg
1

<210> SEQ ID NO 4
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Azido-Phenylalanine
<220> FEATURE:
<221> NAME/KEY: MOD_RES
<222> LOCATION: (4)..(4)
<223> OTHER INFORMATION: 4-aminomethylene-L-phenylalanine modified with
      vinyl sulfone warhead.

<400> SEQUENCE: 4

Phe Leu Leu Phe
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Azido-Phenylalanine
<220> FEATURE:
<221> NAME/KEY: MOD_RES
<222> LOCATION: (4)..(4)
<223> OTHER INFORMATION: 4-aminomethylene-L-phenylalanine modified with
      epoxyketone warhead.

<400> SEQUENCE: 5

Phe Leu Leu Phe
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Azido-Phenylalanine
<220> FEATURE:
<221> NAME/KEY: MOD_RES
<222> LOCATION: (2)..(2)
<223> OTHER INFORMATION: 4-aminomethylene-L-phenylalanine
<220> FEATURE:
<221> NAME/KEY: MOD_RES
<222> LOCATION: (4)..(4)
<223> OTHER INFORMATION: 4-aminomethylene-L-phenylalanine modified with
```

```
       vinyl sulfone warhead.

<400> SEQUENCE: 6

Phe Phe Leu Phe
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with BODIPY-triazole.
<220> FEATURE:
<221> NAME/KEY: MOD_RES
<222> LOCATION: (4)..(4)
<223> OTHER INFORMATION: 4-aminomethylene-L-phenylalanine modified with
       vinyl sulfone warhead.

<400> SEQUENCE: 7

Phe Leu Leu Phe
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Succinyl-Leucine
<220> FEATURE:
<221> NAME/KEY: MOD_RES
<222> LOCATION: (4)..(4)
<223> OTHER INFORMATION: Modified with amino-4-methylcoumarin.

<400> SEQUENCE: 8

Leu Leu Val Tyr
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Modified with amino-4-methylcoumarin.

<400> SEQUENCE: 9

Leu Pro Leu Asp
1

<210> SEQ ID NO 10
<211> LENGTH: 11
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with 7-Methoxycoumarin.
<220> FEATURE:
<221> NAME/KEY: MOD_RES
<222> LOCATION: (10)..(10)
<223> OTHER INFORMATION: Dinitrophenyl-Lysine
<220> FEATURE:
<221> NAME/KEY: MOD_RES
<222> LOCATION: (11)..(11)
<223> OTHER INFORMATION: D-Arg

<400> SEQUENCE: 10

Gly Lys Pro Ile Leu Phe Phe Arg Leu Lys Xaa
1               5                   10

<210> SEQ ID NO 11
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Modified with Rhodamine110.

<400> SEQUENCE: 11

Asp Glu Val Asp
1
```